US008309541B1

(12) United States Patent
Robertson et al.

(10) Patent No.: US 8,309,541 B1
(45) Date of Patent: Nov. 13, 2012

(54) ANTI-CANCER COMPOSITIONS AND METHODS

(75) Inventors: Gavin P. Robertson, Hummelstown, PA (US); SubbRao V. Madhunapantula, Hershey, PA (US); Shantu Amin, Union City, NJ (US); Dhimant Desai, Mechanicsburg, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/107,494

(22) Filed: May 13, 2011

Related U.S. Application Data

(62) Division of application No. 12/423,366, filed on Apr. 14, 2009, now Pat. No. 8,003,633.

(60) Provisional application No. 61/044,788, filed on Apr. 14, 2008.

(51) Int. Cl.
*A01N 43/00* (2006.01)
*A01N 31/00* (2006.01)
*A61K 31/33* (2006.01)
*A61K 31/095* (2006.01)
*C07C 391/00* (2006.01)
*C07C 395/00* (2006.01)

(52) U.S. Cl. .......................... 514/183; 514/706; 562/899
(58) Field of Classification Search .................. 514/183, 514/706; 562/899
See application file for complete search history.

(56) References Cited

U.S. PATENT DOCUMENTS

| | | | |
|---|---|---|---|
| 4,988,517 A | 1/1991 | El-Bayoumy et al. | |
| 5,093,351 A | 3/1992 | Batt | |
| 5,114,969 A | 5/1992 | Chung et al. | |
| 5,231,209 A | 7/1993 | Chung et al. | |
| 5,411,986 A | 5/1995 | Cho et al. | |
| 5,648,097 A | 7/1997 | Nuwayser | |
| 5,929,063 A | 7/1999 | Southan et al. | |
| 5,985,917 A | 11/1999 | Southan et al. | |
| 6,166,003 A | 12/2000 | Lam | |
| 6,465,512 B2 | 10/2002 | Nakamura et al. | |
| 6,511,970 B1 | 1/2003 | Rodriguez | |
| 6,630,486 B1 | 10/2003 | Royer | |
| 6,703,524 B2 | 3/2004 | Lam et al. | |
| 6,737,441 B2 | 5/2004 | Fahey | |
| 7,087,639 B2 | 8/2006 | Lam et al. | |
| 7,314,929 B2 | 1/2008 | Lam et al. | |
| 2002/0165215 A1 | 11/2002 | Lam et al. | |
| 2002/0197304 A1* | 12/2002 | Schrauzer ..................... | 424/449 |

FOREIGN PATENT DOCUMENTS

EP           0750911          1/1997

OTHER PUBLICATIONS

Chiao, J. et al., Ingestion of an Isothiocyanate Metabolite from Cruciferous Vegetables Inhibits Growth of Human Prostate Cancer Cell Xenografts by Apoptosis and Cell Cycle Arrest, *Carcinogenesis*, 25(8):1403-1408, 2004.

Conaway, C. et al., Inhibition of Rat Liver Cytochrome P450 Isozymes by Isothiocyanates and Their Conjugates: a Structure-Activity Relationship Study, *Carcinogenesis*, 17(11):2423-2427, 1996.

Conaway, C. et al., Isothiocyanates as Cancer Chemopreventative Agents: Their Biological Activities and Metabolism in Rodents and Humans, *Current Drug Metabolism*, 3:233-255, 2002.

Jiao, D. et al., Structure-Activity Relationships of Isothiocyanates as Mechanism-based Inhibitors of 4-(Methylnitrosamino)-1-(3-pyridyl)-1-butanone-induced Lung Tumorigenesis in A/J Mice, *Cancer Research*, 54:4327-4333, Aug. 15, 1994.

Misiewicz, M. et al., Sulforaphane and 2-oxyhexyl isothiocyanate Induce Cell Growth Arrest and Apoptosis in L-1210 Leukemia and ME-18 Melanoma Cells, *Oncol. Rep.*, 10(6):2045-2050, 2003 (Absract).

Morse, M. et al., Structure-Activity Relationships for Inhibition of 4-(Methylnitrosamino)-1-(3-pyridyl)-1-butanone Lung Tumorigenesis by Arylalkyl Isothiocyanates in A/J Mice, *Cancer Research*, 51:1846-1850, Apr. 1, 1991.

Sasaki, T. et al., Effects of Isothiocyanates on Growth and Metastaticity of B16-F10 Melanoma Cells, *Nutr. Cancer*, 33(1):76-81, 1999.

Stoner, G. et al., Isothiocyanates and Freeze-Dried Strawberries as Inhibitors of Esophageal Cancer, *Toxicological Sciences*, 52 (Supp): 95-100, 1999.

Xiao, D. et al., Allyl Isothiocyanate, a Constituent of Cruciferous Vegetables, Inhibits Proliferation of Human Prostate Cancer Cells by Causing G2/M Arrest and Inducing Apoptosis, *Carcinogenesis*, 24(5):891-897, 2003.

Tanaka, T. et al., Suppressing Effects of Dietary Supplementation of the Organoselenium 1,4-Phenylenebis(methylene)selenocyanate and the *Citrus* Antioxidant Auroptene on Lung Metastasis of Melanoma Cells in Mice, *Cancer Research*, 60: 3713-3716, Jul. 15, 2000.

Reddy, B. et al., Chemoprevention of Colon Cancer by Organoselenium Compounds and Impact of High- or Low-Fat Diets, *Journal of the National Cencer Institute*, 89(7): 506-518. Apr. 2, 1997.

(Continued)

*Primary Examiner* — Samira Jean-Louis
(74) *Attorney, Agent, or Firm* — Gifford, Krass, Sprinkle, Anderson & Citkowski, P.C.

(57) ABSTRACT

Anti-cancer compositions and methods are described including one or more compounds having the structural formula I: R2-R-R1, where R is phenyl, where R1 is $(CH_2)_n Se-C(=NH)-NH_2$, where R2 is $(CH_2)_n Se-C(=NH)-NH_2$ or R2 is H, and where each n is independently 2, 3, 4, 5, 6, 7, or 8. Methods of treating a subject are provided according to embodiments of the present invention which include administering a therapeutically effective amount of a composition including one or more compounds having the structural formula I to a subject having a condition characterized by Akt dysregulation. Administering a therapeutically effective amount of a composition including one or more compounds having the structural formula I to a subject detectably increases apoptosis and/or decreases proliferation of cancer cells, particularly cancer cells characterized by Akt dysregulation. Compositions of the present invention inhibit Akt enzymes, iNOS, and increase MAP kinase activity such that cancer cells contacted with the compositions are inhibited.

8 Claims, 17 Drawing Sheets

OTHER PUBLICATIONS

Rao, C. et al., Chemoprevention of Colon Cancer by a Glutathione Conjugate of 1,4-Phenylenebis(methylene)selenocyanate, a Novel Organoselenium Compound with Low Toxicity, Cancer Research, 61: 3647-3652, May 1, 2001.
Reddy, B. et al., Chemoprevention of Colon Cancer by the Synthetic Organoselenium Compound 1,4-Phenylenebis(methylene)selenocyanate, Cancer Research, 52: 5635-3540, Oct. 15, 1992.
Conaway, C. et al., Phenethyl Isothiocyanate and Sulforaphane and their N-Acetylcysteine Conjugates Inhibit Malignant Progression of Lung Adenomas Induced by Tobacco Carcinogens in A/J Mice, Cancer Research, 65(1): 8548-8557, Sep. 15, 2005.
Jiao, D. et al., Chemopreventive activity of thiol conjugates of isothiocyanates for lung tumorigenesis, Carcinogenesis, 18(11):2143-2147, 1997.
West, K. et al., Rapid Akt activation by nicotine and a tobacco carcinogen modulates the phenotype of normal human airway epithelial cells, The Journal of Clinical Investigation, 111(1): 81-90, Jan. 2003.
El-Bayoumy, K. et al., Cancer Chemoprevention by Garlic and Garlic-Containing Sulfur and Selenium Compounds, The Journal of Nutrition, pp. 864S-869S, 2006.
Garvey, E. et al., Potent and Selective Inhibition of Human Nitric Oxide Syntheses, The Journal of Biological Chemistry, 269(43): 26669-26676, Oct. 28, 1994.
Fernandez-Bolanos, J. et al., Synthesis of O-unprotected glycosyl selenoureas. A New access to bicyclic sugar isoureas, Tetrahedron Letters, 45: 4081-4084, 2004.
Datta, S. et al., Cellular survival: a play in three Akts, Genes & Development, 13: 2905-2927, 1999.
Fayard, E. et al., Protein Kinase B/Akt at a Glance, Journal of Cell Science, 118(24): 5675-5678, Dec. 15, 2005.
Testa, J. et al., AKT plays a central role in tumorigenesis, PNAS, 98(20): 10983-10985, Sep. 25, 2001.
Stahl JM, et al., Deregulated Akt3 activity promotes development of malignant melanoma. Cancer Research, 64:7002-10, Oct. 1, 2004.
Stahl JM, et al., Loss of PTEN Promotes Tumor Development in Malignant Melanoma, Cancer Research, 63:2881-90, Jun. 1, 2003.
Marani, A. et al., New Synthesis Method of Polythiophenes, Iranian Jouranl of Polymer Science and Technology, 3(1): 2-12, Jan. 1994.
Rao, C. et al., Chemoprevention of colonic aberrant crypt foci by an inducible nitric oxide synthase-selective inhibitor, Carcinogenesis, 20(4): 1-644, 1999.
Crowell, J. et al., Is Inducible Nitric Oxide Synthase a Target for Chemoprevention?, Molecular Cancer Therapeutics, 2: 815-823, Aug. 2003.
Chen, T. et al., Chemopreventive Effects of a Selective Nitric Oxide Synthase Inhibitor on Carcinogen-Induced Rate Esophageal Tumorigenesis, Cancer Research, : 3714-3717, May 15, 2004.
Ip, C., Comprison of selenium and sulfur analogs in cancer prevention, Carcinogenesis, 13(7): 1167-70, Jul. 1992.
Das, R., et al., Amelioration of benzo (a) pyrene-induced lung carcinogenesis in strain A mice by diphenylmethyl selenocyanate, Experimental and Toxicologic Pathology, 58: 351-360, 2007.
Helmbach, H. et al., Drug-Resistance in Human Melanoma, International Journal of Cancer, 93: 617-622, 2001.
Markovic, S., et al., Malignant Melanoma in the 21st Century, Part 1: Epidemiology, Risk Factors, Screening, Prevention, and Diagnosis, Mayo Clinic Proceedings, 82(3): 364-380, Mar. 2007.
Amiri, K. et al., Augmenting Chemosensitivity of Malignant Melanoma Tumors via Proteasome Inhibition: Implication for Bortezomib (VELCADE, PS-341) as a Therapeutic Agent for Malignant Melanoma, Cancer Research, 64:4912-4918, 2004.
Madhunapantula, S. et al., PRAS0 Deregulates Apoptosis in Malignant Melanoma, Cancer Research, 67: 3626-36, 2004.
Zhang, Y., et al., Anticarcinogenic activities of sulforaphane and structurally related synthetic norbornyl isothiocyanates, Proceedings of National Academy of Sciences of the USA, 91: 3147-50, 1994.
Zhang, Y. et al., Vegetable-derived isothiocyanates: anti-proliferative activity and mechanism of action, Proceedings of the Nutrition Society, 65: 68-75, 2006.

Miyoshi, N. et al., A Link Between Benzyl Isothiocyanate-Induced Cell Cycle Arrest and Apoptosis: Involvement of Mitogen-Activated Protein Kinases in the Bcl-2 Phosphorylation, Cancer Research, 64: 2134-2142, Mar. 15, 2004.
Yang, L. et al., Akt/Protein Kinase B Signaling Inhibitor-2, a Selective Small Molecule Inhibitor of Akt Signaling with Antitumor Activity in Cancer Cells Overexpressing Akt, Cancer Research, 64: 4394-4399, Jul. 1, 2004.
Karst, A. et al., Role of p53 Up-regulated Modulator of Apoptosis and Phosphorylated Akt in Melanoma Cell Growth, Apoptosis, and Patient Survival, Cancer Research, 66(18): 9221-9226, Sep. 15, 2006.
Hu, H. et al., PKB/AKT and ERK regulation of caspase-mediated apoptosis by methylseleninic acid in LNCaP prostate cancer cells, Carcinogenesis, 26(8): 1374-1381, 2005.
Unni, E. et al., Se-methylselenocysteine inhibits phosphatidylinositol 3-kinase activity of mouse mammary epithelial tumor cells in vitro, Breast Cancer Research, 7: R699-R707, 2005.
Krishan, A., Rapid flow cytofluorometric analysis of mammalian cell cycle by propidium iodide staining, Journal of Cell Biology, 66: 188-193, 1975.
Hecht, S., Chemoprevention by Isothiocyanates, Cancer Chemopreventative, 1:21-35, 1995.
Salvucci, O. et al., Antiapoptotic Role of Endogenous Nitric Oxide in Human Melanoma Cells, Cancer Research, 61: 318-326, Jan. 1, 2001.
Ekmekcioglu, S. et al., Inducible Nitric Oxide Synthase and Nitrotyrosine in Human Metastatic Melanoma Tumors Correlate with Poor Survival, Clinical Cancer Research, 6: 4768-4775, Dec. 2000.
Ekmekcioglu, S. et al., Tumor iNOS predicts poor survival for stage III melanoma patients, International Journal of Cancer, 119: 861-866, 2006.
Madhunapantula, S. et al., Is B-Raf a Good Therapeutic Target for Melanoma and Other Malignancies?, Cancer Research, 68(1): 5-8, Jan. 1, 2008.
Lang, J. et al., Absence of Exon 15 BRAF Germline Mutations in Familial Melanoma, Human Mutation, 21: 327-330, 2003.
Davies, H. et al., Mutations of the BRAF Gene in Human Cancer, Nature, 417: 949-954, Jun. 27, 2002.
Cheung, M. et al., Akt and Mutant $^{V600}$EB-Raf Cooperate to Prormote Early Melanoma Development, Cancer Research, 68(9): 3429-3439, May 1, 2008.
Sharma, A. et al., Target Mitogen-Activated Protein Kinase/Extracellular Signal-Regulated Kinase Kinase in the Mutant (V600E) B-Raf Signaling Cascade Effectively Inhibits Melanoma Lung Metastases, Cancer Research, 66(16): 8200-09, Aug. 15, 2006.
Sharma, A. et al., Mutant $^{V599E}$B-Raf Regulates Growth and Vascular Development of Malignant Melanoma Tumors, Cancer Research, 65(6): 2412-2421, Mar. 15, 2005.
Jemal, A. et al., Cancer Statistics 2002, Cancer Journal for Clinicians, 52: 23-47, 2002.
Grossman D, et al., Drug resistance in melanoma: mechanisms, apoptosis, and new potential therapeutic targets. Cancer & Metastasis Reviews 2001; 20:3-11.
Gray-Schopfer V, et al., Melanoma biology and new targeted therapy. Nature 2007;445:851-857.
Brazil DP, et al., Ten years of protein kinase B signalling: a hard Akt to follow. Trends Biochem Sci 2001;26:657-64.
Nicholson KM, The protein kinase B/Akt signalling pathway in human malignancy. Cell Signal 2002;14:381-95.
Keum Ys, et al., Chemoprevention by isothiocyanates and their underlying molecular signaling mechanisms. Mutat Res 2004;555:191-202.
Zhang Y., Cancer-preventive isothiocyanates: measurement of human exposure and mechanism of action. Mutat Res 2004;555:173-90.
Ji Y, et al., Pharmacokinetics of dietary phenethyl isothiocyanate in rats. Pharm Res 2005;22:1658-66.
Robertson, G.P., Functional and therapeutic significance of Akt deregulation in malignant melanoma, Cancer Metastasis Rev., 2005, 24:273-85.

Rao, C.V., Nitric oxide signaling in colon cancer chemoprevention, Mutat. Res., 2004;555:107-19.

Misko, T.P. et al., Selective inhibition of the inducible nitric oxide synthase by aminoguanidine, Eur J. Pharmacol., 1993;233:119-25.

Tunctan B, et al., Inhibition of extracellular signal-regulated kinase (ERK1/2) activity reverses endotoxin-induced hypotension via decreased nitric oxide production in rats, Pharmacol. Res., 2007, 56:56-64.

Michaloglou, C. et al., BRAFE600-associated senescence-like cell cycle arrest of human naevi, Nature, 2005, 436:720-4.

Dhomen, N. et al., Oncogenic Braf induces melanocyte senescence and melanoma in mice, Cancer Cell, 2009, 2009, 15, 294-303.

Jakubikova, J. et al., Role of PI3K/Akt and MEK/ERK signaling pathways in sulforaphane- and erucin-induced phase II enzymes and MRP2 transcription, G2/M arrest and cell death in Caco-2 cells, Biochemical Pharmacology, 69(11): 1543-52, Jun. 1, 2005.

Xu, K. et al., Studies on the mechanism of the inhibition of human leukaemia cell growth by dietary isothiocyanates and their cysteine adducts in vitro, Biochemical Pharmacology, 60(2): 221-31, Jul. 15, 2000.

Serrone L, et al., The chemoresistance of human malignant melanoma: and update, *Melanoma Research*, 9: 51-58, 1999.

Reinhold U, et al., Serum selenium levels in patients with malignant melanoma, *Acta Derm Veroel*, 69:132-136, 1989.

Feun L, et al., A phase II trial of tricyclic nucleoside phosphate in patients with advanced squamous cell carcinoma of the cervix, *American Journal of Clinical Oncology*, 16(6):506-508, 1993.

Massi D, et al., Inducible nitric oxide synthase expression in benign and malignant cutaneous melanocytic lesions, *Journal of Pathology*, 194: 194-200, 2001.

Zheng M, et al., WP760, a melanoma selective drug, *Cancer Chemother Pharmacol*, 60: 625-633, 2007.

Ellerhorst JA, et al., Regulation of iNOS by the p44/42 mitogen-activated protein kinase pathway in human melanoma, *Oncogene*, 25: 3956-3962, 2006.

Manesh C, et al., Effect of naturally occurring allyl and phenyl isothiocyanates in the inhibition of experimental pulmonary metastasis induced by B16F-10 melnoma cells, *Fitoterapia*, 74:355-363, 2003.

Jakubikova J, et al., Effects of MEK1 and PI3K inhibitors on allyl-, benzyl- and phenylethyl-isothiocyanate-induced $G_2$/M arrest and cell death in Caco-2 cells, *International Journal of Oncology*, 27(5): 1449-1458, 2005.

Morse M, et al., Effects of alkyl chain length on the inhibition of NNK-induced lung neoplasia in A/J mice by arylalkyl isothiocyanates, *Carcinogenesis*, 10(9):1757-1759, 1989.

Bandura, L. et al., Differential effects of selenite and selenate on human melanocytes, keratinocytes, and melanoma cells, *Biochemistry and Cell Biology*, 83: 196-211, 2005.

Brigelius-Flohe, R., Selenium Comppunds and Selenoproteins in Cancer, *Chemistry & Biodiversity*, 5:389-395, 2008.

S. Madhunapantula et al., Development of a novel iNOS inhibitor that retards melanoma metastasis, Abstract online, Mar. 12, 2007.

S. Madhunapantula et al., A Novel Selenium Analog of the iNOS Inhibitor Retards Melanoma Tumor Development, 2007 AACR Annual Meeting, Los Angeles, CA, Apr. 15, 2007.

A. Sharma et al., Identification of small molecule inhibitors that target Akt3 signaling in melanoma, Abstract online, Mar. 12, 2007.

A. Sharma et al., Identification of small molecule inhibitors that target Akt3 signaling in melanoma, 2007 AACR Annual Meeting, Los Angeles, CA, Apr. 16, 2007.

D. Desai et al., Chemopreventive and therapeutic efficacy of a new selective nitric oxide synthase inhibitor on melanoma lung metastasis, Abstract online, Mar. 12, 2007.

A. Sharma et al., Synthesis and biological activity comparison of isoselenocyanates with isothiocyanate present in cruciferous vegetables, Abstract online, Mar. 12, 2007.

A. Sharma et al., Synthesis and biological activity comparison of isoselenocyanates with isothiocyanate present in cruciferous vegetables, 2007 AACR Annual Meeting, Los Angeles, CA, Apr. 16, 2007.

Chen, T. et al., Chemopreventive Effects of a Selective Nitric Oxide Synthase Inhibitor on Carcinogen-Induced Rate Esophageal Tumorigenesis, *Cancer Research* 64: 3714-3717, May 15, 2004.

Zhang, Y., et al Anticarcinogenic activities of sulforaphane and structurally related synthetic norbornyl isothiocyanates, *Proceedings of National Academy of Sciences of the USA*, 91: 3147-50, 1994.

Hu, H, et al., PKB/AKT and ERK regulation of caspase-mediated apbptosis by methylseleninic acid in LNCaP prostate cancer cells, *Carcinogenesis*, 26(8): 1374-1381, 2005.

Hecht, S., Chemoprevention by Isothiocyanates, *Cancer Chemopreventalive*, 1: 21-35, 1995.

Jakubikova, J. et al., Role of PI3K/Akt and MEK/ERK signaling pathways in sulforaphane- and erucin-induced phase II enzymes and MRP2 transcription, G2/M arrest and cell death in Caco-2 cells, Biochemical Pharmacology, 69(11): 1543-52, Jun. 1, 2005.

Jakubikova J, et al., Effects of MEK1 and PI3K inhibitors on allyl-, benzyl- and phenylethyl-isothiocyanate-induced $G_2$/M arrest and cell death in Caco-2 cells, *International Journal of Oncology*, 27(5): 1449-1458, 2005.

Chiao, J. et al., Ingestion of an Isothiocyanate Metabolite from Cruciferous Vegetables Inhibits Growth of Human Prostate Cancer Cell Xenografts by Apoptosis and Cell Cycle Arrest, *Carcinogenesis*, 25(8)1403-1408, 2004.

Morse, M. et al, Structure-Activity Relationships for Inhibition of 4-(Methylnitrosamino)-1-(3-pyridyl)-1-butanone Lung Tumorigenesis by Arylalkyl Isothiocyanates in A/J Mice, *Cancer Research*, 51:1846-1850, Apr. 1, 1991.

* cited by examiner

Figure 1
A Structures
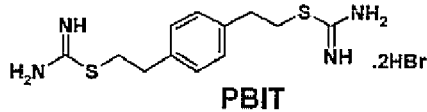
PBIT
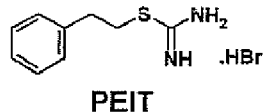
PEIT
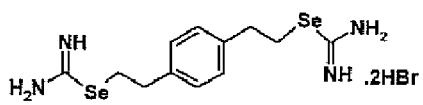
PBISe
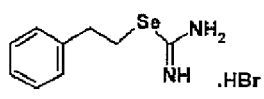
PEISe
B Caco-2 Cell viability (MTS assay)
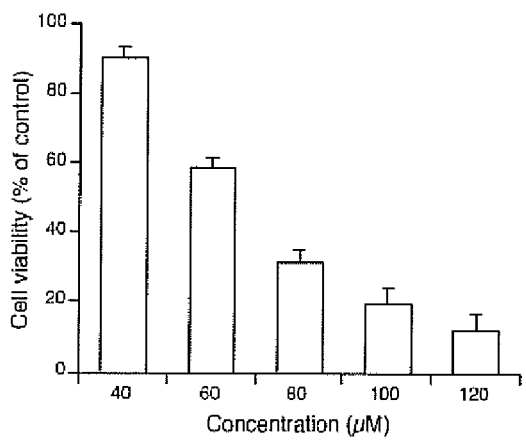
PBIT ($IC_{50}$ = 59.44 ± 3.83 µM)
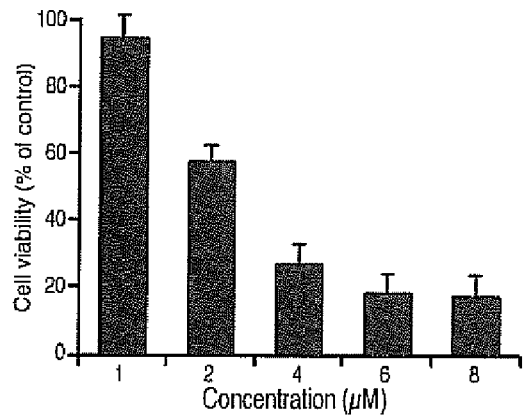
PBISe ($IC_{50}$ = 2.4 ± 0.4 µM)
C Caco-2 Nitrite quantitation
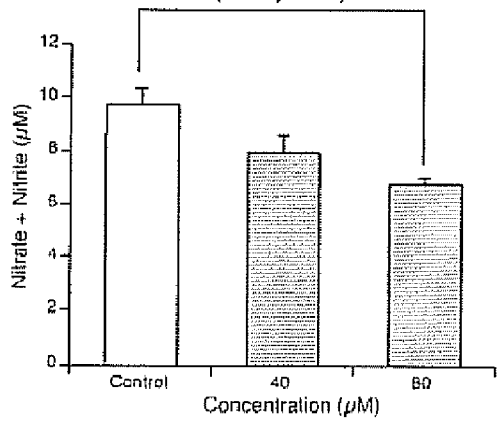
PBIT
$P < 0.05$
(One-way ANOVA)
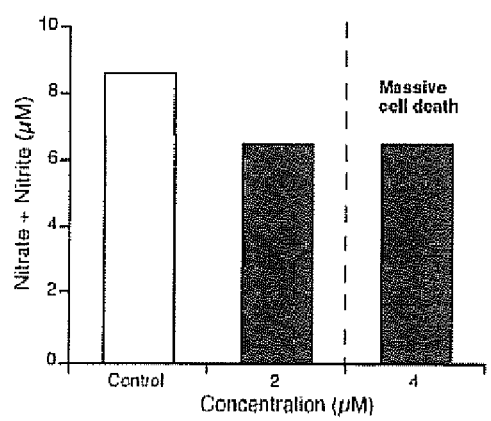
PBISe

Figure 2

A UACC 903 cell viability (MTS assay)

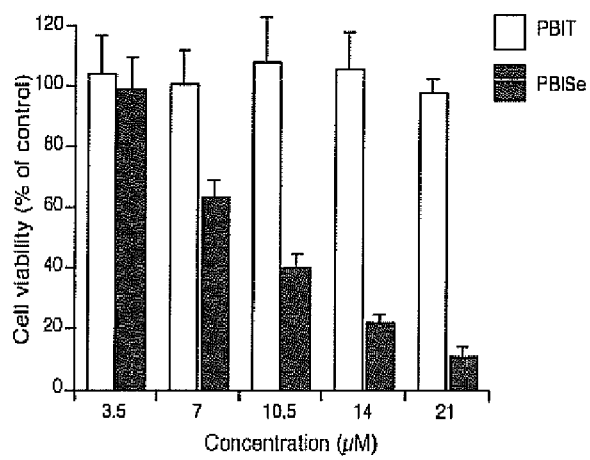

B Comparison of PBISe IC$_{50}$ (μM) values between melanoma cells and normal human fibroblasts

| Treatment time (hours) | Human fibroblast cells (FF244.1) | Human metastatic melanoma cells (UACC 903) | Fold Difference |
|---|---|---|---|
| 4 | 77.76 | 37.64 | 2.06 |
| 6 | 75.85 | 14.71 | 5.16 |
| 12 | 26.59 | 11.58 | 2.29 |
| 24 | 17.08 | 7.78 | 2.19 |

PBISe inhibits melanoma proliferation at concentrations 2-5 fold lower than human fibroblast cells

C UACC 903 BrdU incorporation

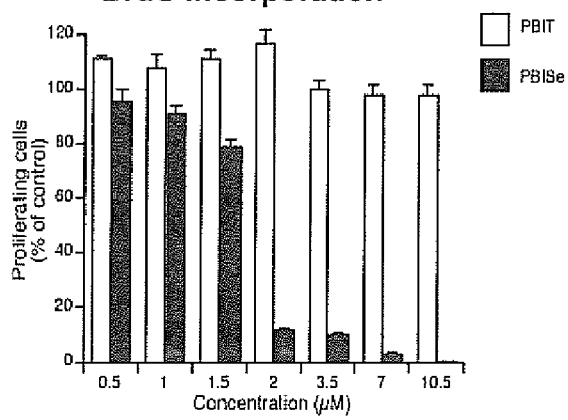

D UACC 903 Caspase-3/7 activity

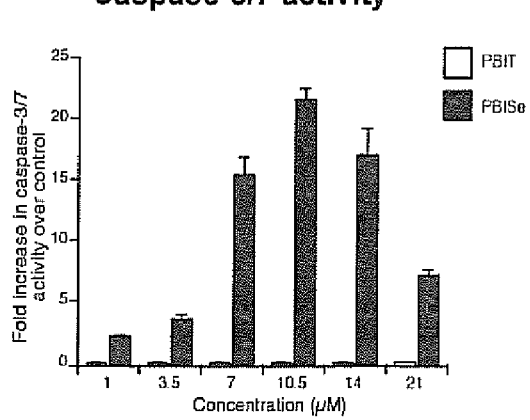

Figure 3
A   UACC 903 sub G0/G1 cell population
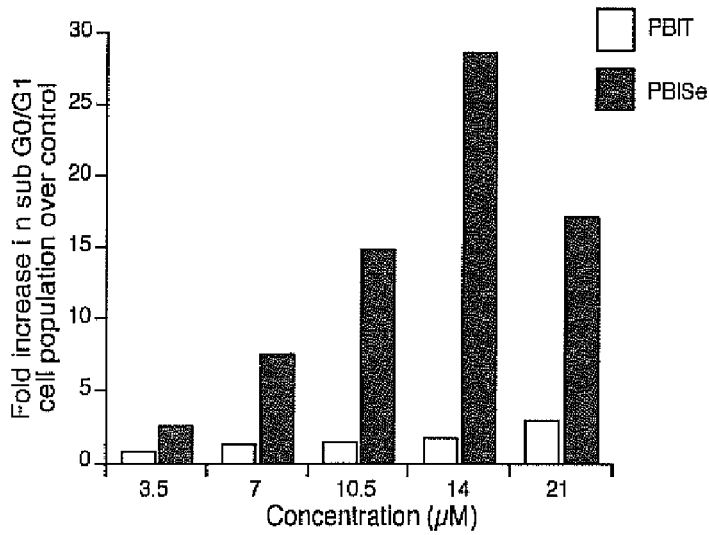
B   UACC 903 G2/M cell population
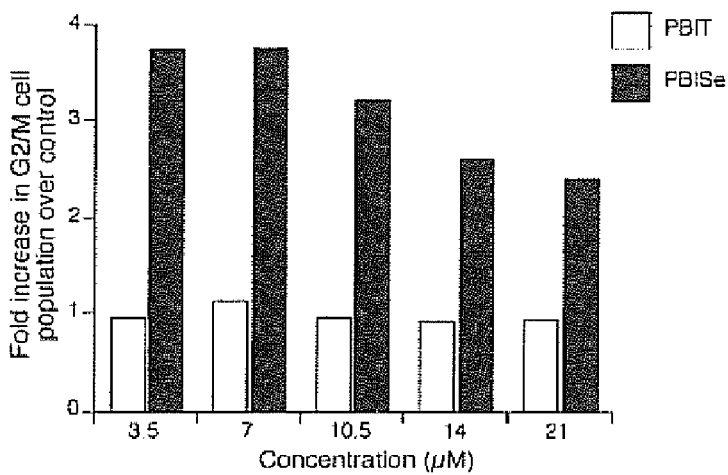
C   Effect of PBISe and PBIT treatment on UACC 903 cell cycle
|  | DMSO | PBIT | | | | | PBISe | | | | |
|---|---|---|---|---|---|---|---|---|---|---|---|
| Concentration (μM) |  | 3.5 | 7 | 10.5 | 14 | 21 | 3.5 | 7 | 10.5 | 14 | 21 |
| G0/G1 (%) | 58.0 | 59.40 | 60.3 | 60.1 | 62.4 | 63.0 | 52.7 | 47.0 | 48.0 | 53.0 | 53.0 |
| S (%) | 32.0 | 31.10 | 29.0 | 30.5 | 29.0 | 28.0 | 10.0 | 16.0 | 20.0 | 21.0 | 23.3 |
| G2/M (%) | 10.0 | 9.45 | 11.0 | 9.4 | 9.00 | 9.10 | 37.3 | 37.5 | 32.0 | 26.0 | 24.0 |

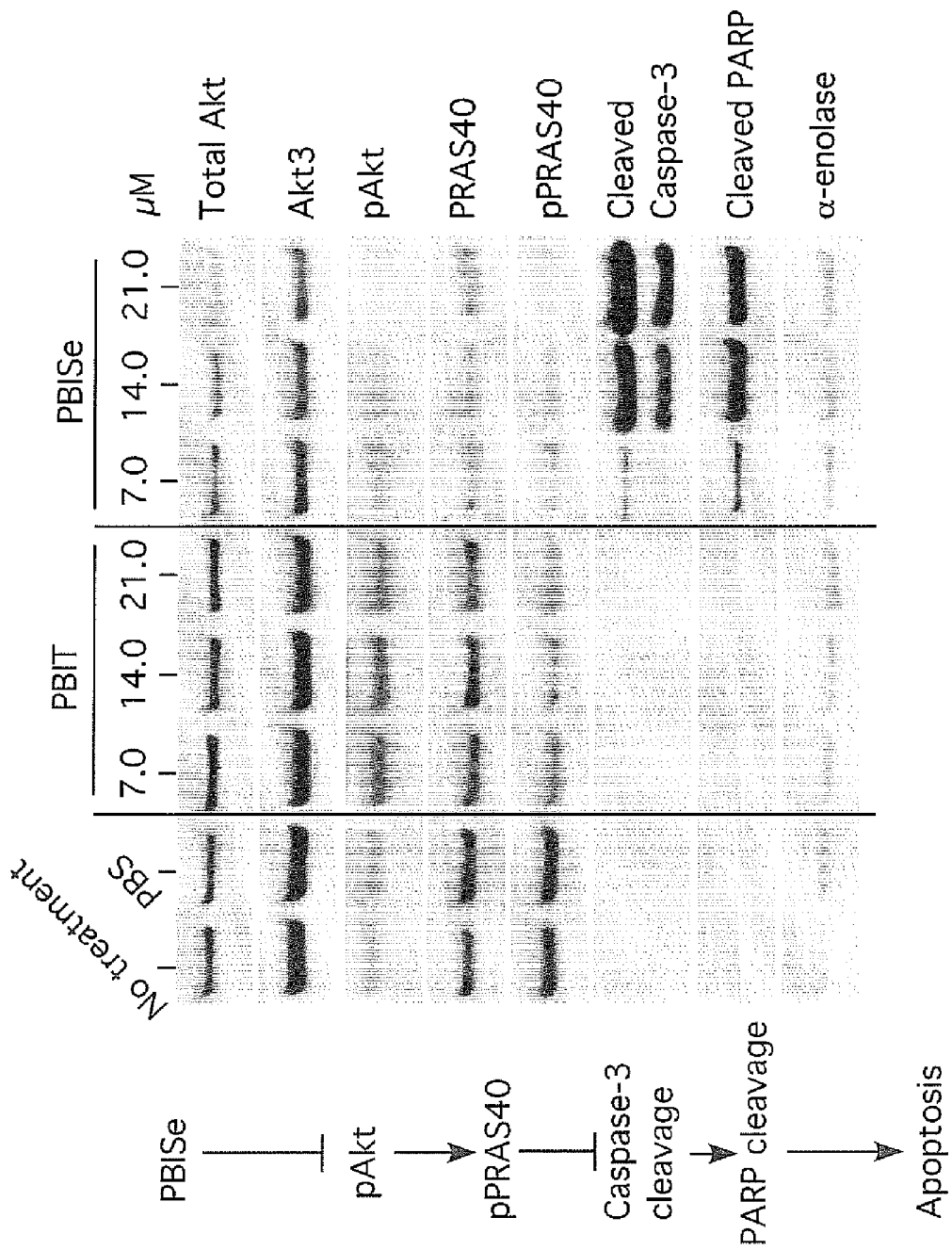

pErk1/2 and iNOS pathway

Cell proliferation signaling

1205 Lu tumor kinetics

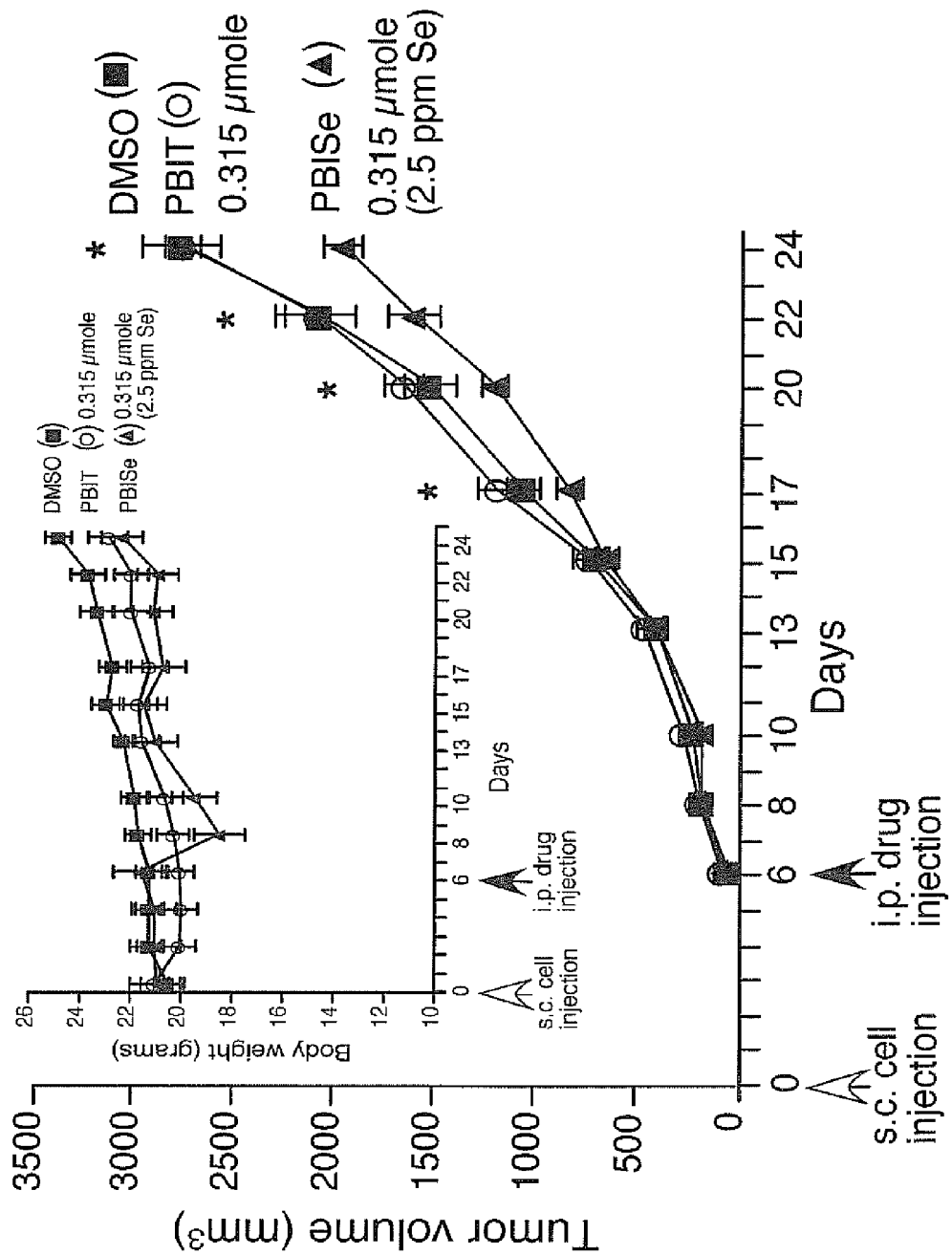

Toxicity analysis

Caspase-3/7 activity analysis

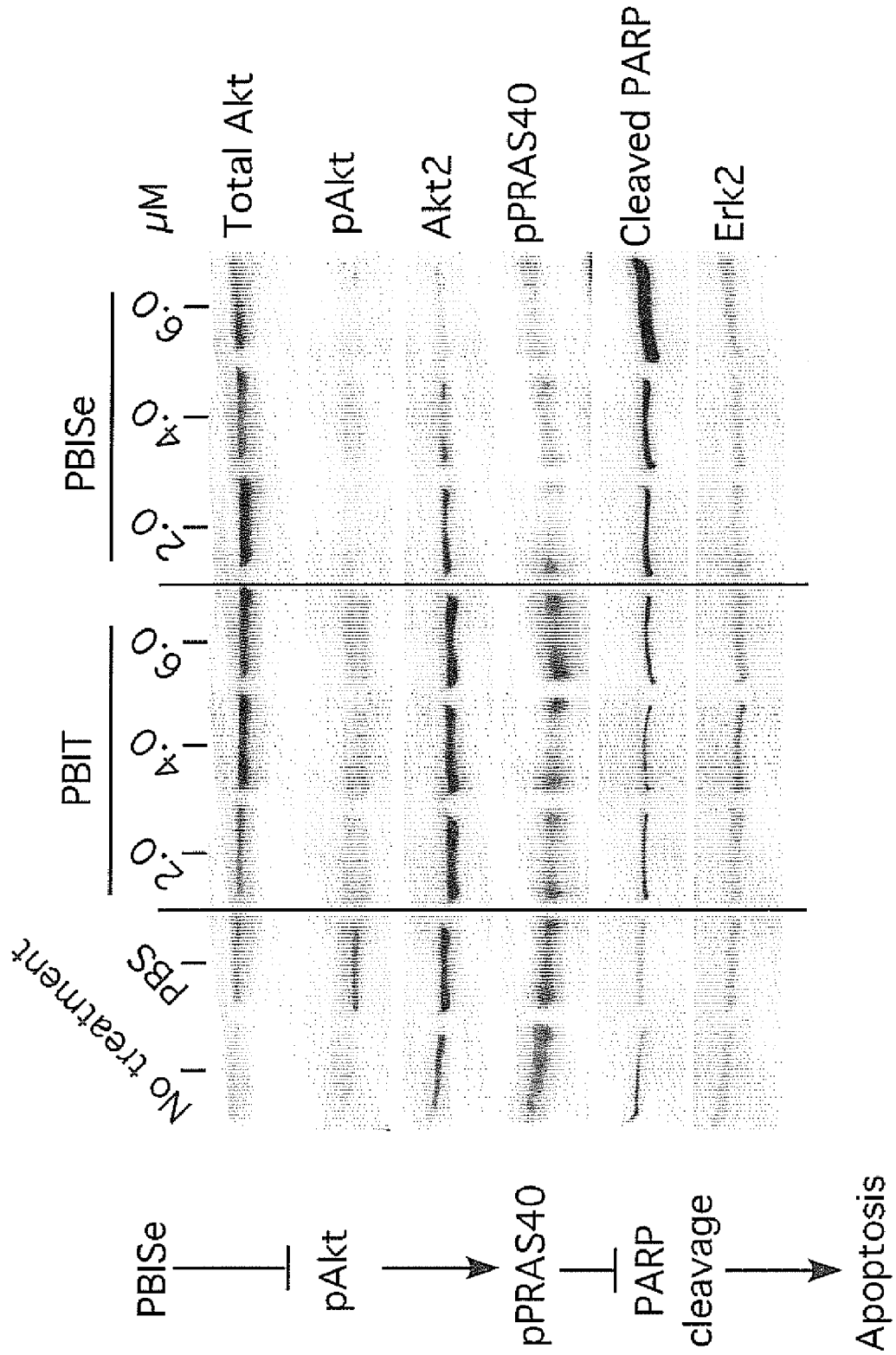

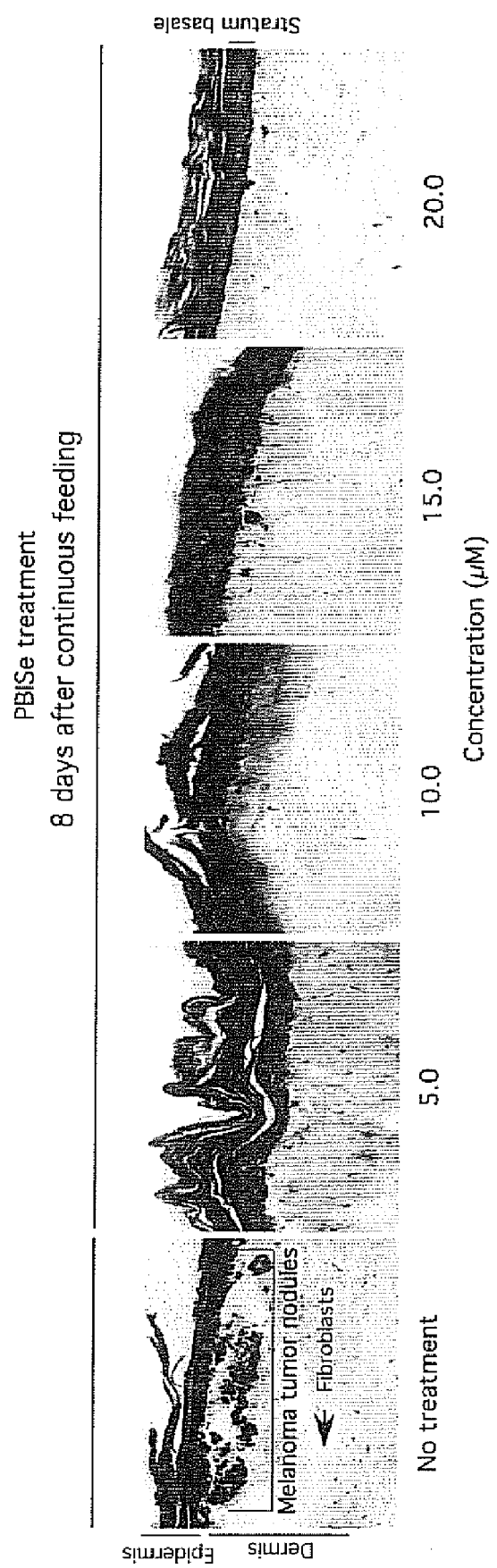

Figure 7B
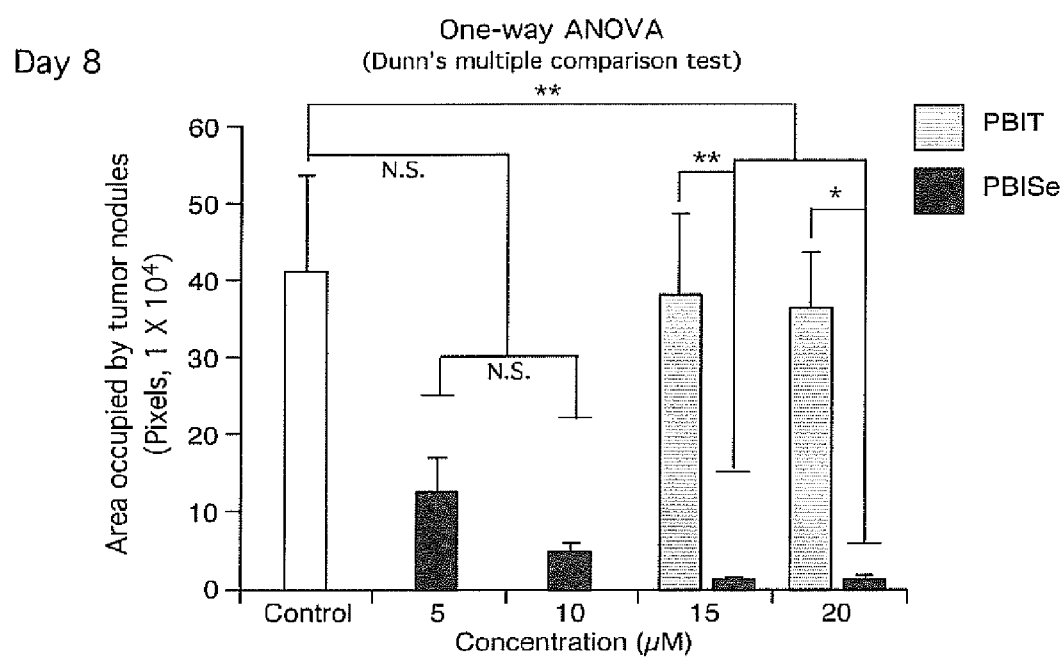
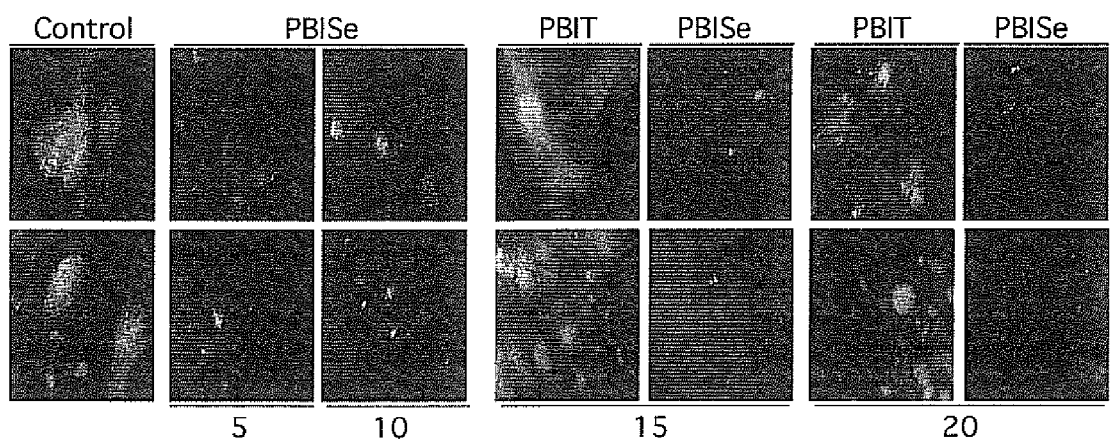

Figure 7C
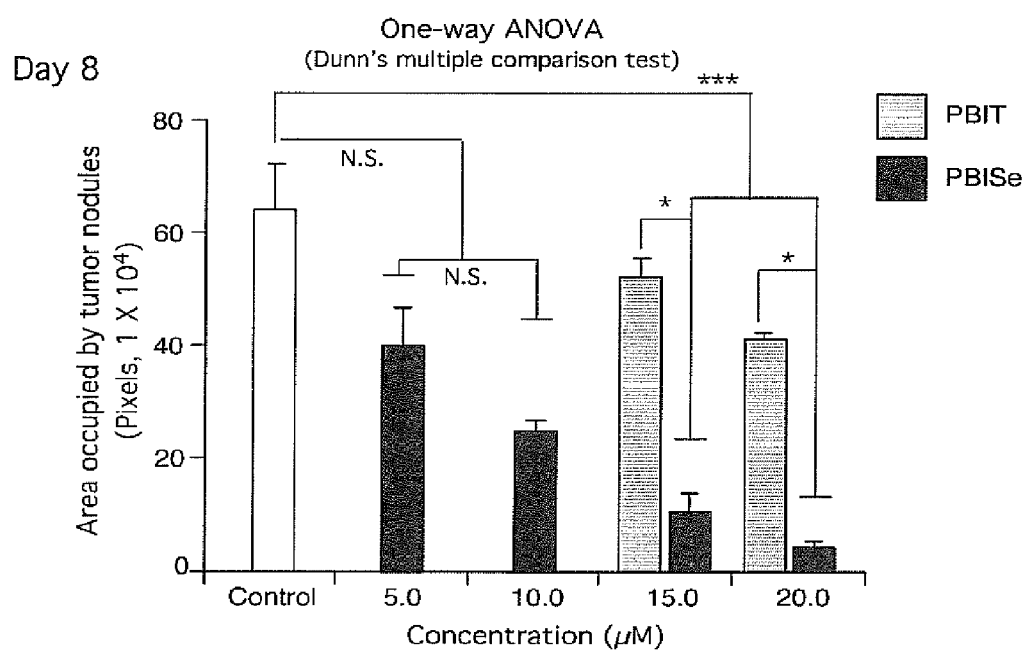
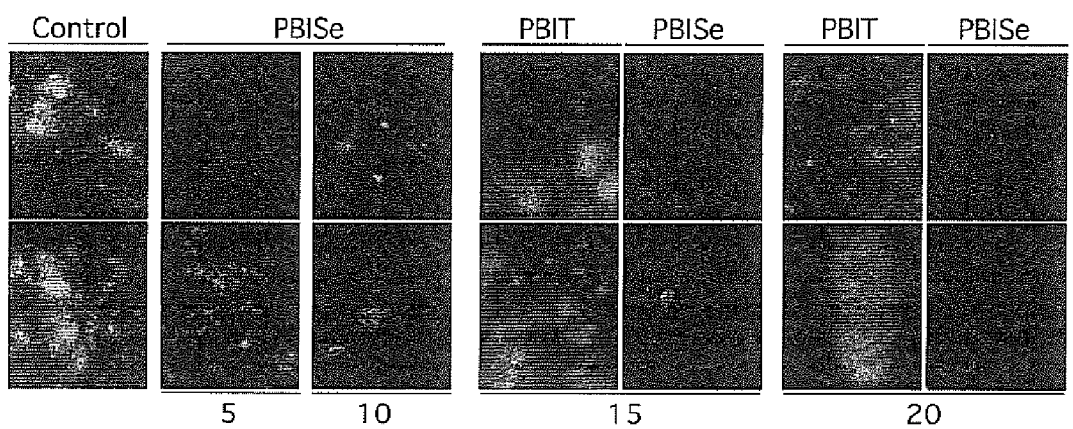

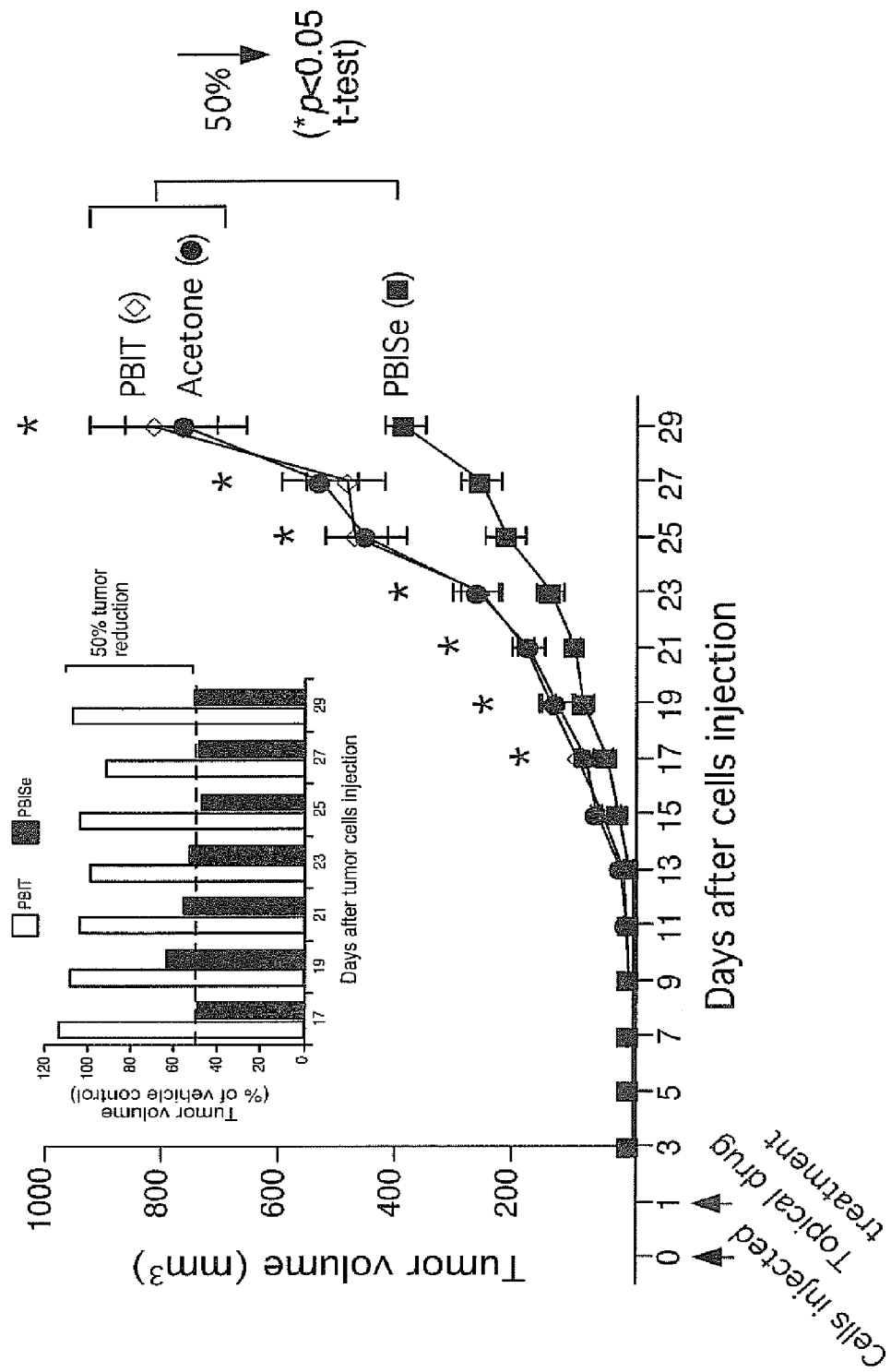

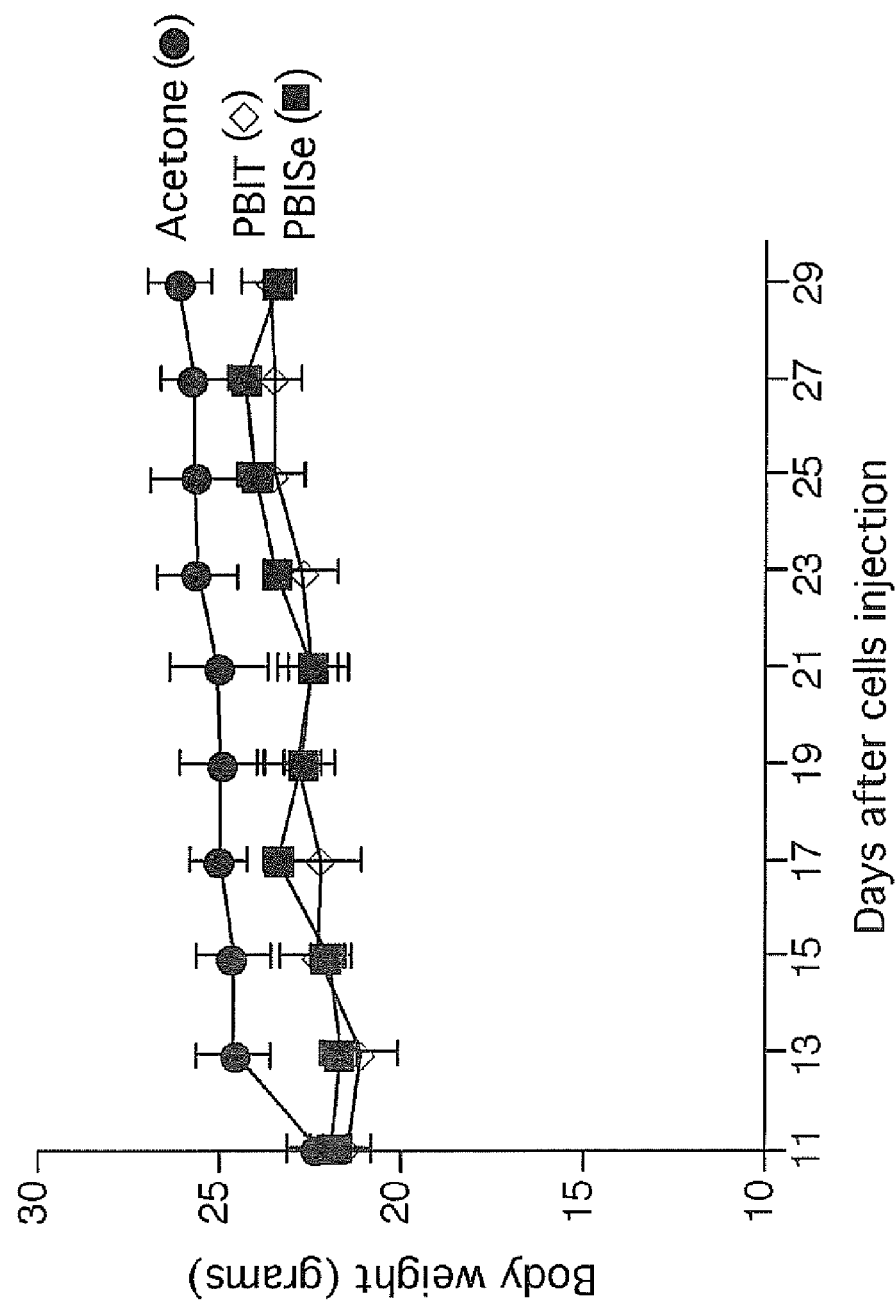

Figure 8C

|  | Vehicle | PBIT | PBISe | Marker for |
|---|---|---|---|---|
| SGOT (AST) (Units/L) (59 – 247) | 171.9 ± 30.2 | 218.6 ± 27.2 | 270.5 ± 43.7 | Liver toxicity |
| SGPT (ALT) (Units/L) (28 – 132) | 48.6 ± 6.7 | 76 ± 31.5 | 103.7 ± 21.5 | Liver and bile duct damage |
| Alkaline phosphatase (ALP) (Units/L) (62 – 209) | 68.5 ± 11.9 | 81.3 ± 15.2 | 70.4 ± 12.8 | Liver and kidney toxicity and bile duct damage |

|  | Vehicle | PBIT | PBISe | Marker for |
|---|---|---|---|---|
| Blood glucose (mg/dL) (90 – 192) | 212.9 ± 10.6 | 216.2 ± 11.0 | 238.8 ± 23.7 | Metabolic activity; liver pancreatic function |
| Creatinine (mg/dL) (0.2 – 0.8) | 0.29 ± 1.4 | 0.20 ± 0.0 | 0.18 ± 1.7 | Kidney function |
| Blood urea nitrogen (BUN) (mg/dL) (18 – 29) | 31 ± 0 | 17.3 ± 1.9 | 19 ± 1.6 | Kidney function |
| Total protein (g/dL) (3.6 – 6.6) | 5.5 ± 0.15 | 5.3 ± 0.18 | 5.7 ± 0.12 | Metabolic activity, liver and kidney function |

ANTI-CANCER COMPOSITIONS AND METHODS

REFERENCE TO RELATED APPLICATIONS

This application is a divisional of U.S. patent application Ser. No. 12/423,366, filed Apr. 14, 2009, which claims priority from U.S. Provisional Patent Application Ser. No. 61/044,788 filed Apr. 14, 2008, the entire content of both of which is incorporated herein by reference.

GOVERNMENT SPONSORSHIP

The invention was made with government support under Contract No. HHSN261200566003C awarded by the U.S. Public Health Service; Contract No. NO2-CB-56603 awarded by the U.S. National Institutes of Health National Cancer Institute; and Contract No. CA-127892-01A awarded by the U.S. National Institutes of Health. The government has certain rights in the invention.

FIELD OF THE INVENTION

The present invention relates generally to anti-cancer compositions and methods. In specific embodiments, the present invention relates to compositions including one or more selenium-containing compounds, methods for treatment and/or prevention of pathological conditions in a subject using one or more selenium-containing compounds and methods for synthesis of particular selenium-containing compounds.

BACKGROUND OF THE INVENTION

In spite of recent medical progress, cancer continues to be one of the most common and deadly diseases. Elucidation of biochemical pathways involved in development and progression of various cancers is important to identify potential anti-cancer treatments as well as to develop agents effective to regulate such pathways in other aspects of health and disease.

Akt kinase family members, Akt1/PKBα, Akt2/PKBβ or Akt3/PKBγ, play important roles in development of a large variety of cancers including melanoma (Robertson, G. P., Cancer Metastasis Rev., 2005, 24:273-85; Stahl, J. M. et al., Cancer Res., 2004, 64:7002-10.)

A particular cancer, melanoma, is the most deadly form of skin cancer due to its high metastatic potential. Akt3 and downstream PRAS40 are part of a key signaling cascade activated in ~70% of melanomas. Akt3 functions to reduce cellular apoptosis in early melanomas, thereby promoting development of this disease.

Inducible Nitric Oxide Synthase (iNOS) deregulation is associated with cancers, including melanoma, and is correlated with poor survival. iNOS is a calcium independent, cytokine-inducible enzyme involved in production of a bioactive, pleiotropic regulatory and signaling molecule from arginine called nitric oxide (Rao, C. V., Mutat. Res., 2004; 555:107-19.) Among other cancers, recent studies have implicated iNOS as a potential therapeutic target in melanoma (Ekmekcioglu, S. et al., Clin. Cancer Res., 2000, 6:4768-75; Ekmekcioglu, S. et al., Int J Cancer 2006; 119: 861-6; Massi, D. et al., J. Pathol., 2001; 194:194-200; Salvucci, O. et al., Cancer Res., 2001, 61:318-26.)

Among the three isoforms of NOS, calcium independent iNOS produces high levels of nitric oxide promoting development of a malignant phenotype (Rao, C. V., Mutat. Res., 2004; 555:107-19; Ekmekcioglu, S. et al., Clin. Cancer Res., 2000, 6:4768-75; Ekmekcioglu, S. et al., Int J Cancer 2006; 119:861-6; Salvucci, O. et al., Cancer Res., 2001, 61:318-26.) Elevated iNOS expression/activity is also correlated with poor survival rates of melanoma patients (Ekmekcioglu, S. et al., Clin. Cancer Res., 2000, 6:4768-75; Ekmekcioglu, S. et al., Int J Cancer 2006; 119:861-6)

A number of small molecule iNOS inhibitors have been identified and tested in vitro and in viva (Rao, C. V., Mutat. Res., 2004, 555:107-19; Misko, T. P. et al., Eur J. Pharmacol., 1993; 233:119-25; Zheng, M. et al., Cancer Chemother Pharmacol 2007, 60:625-33; Garvey, E. P. et al., J. Biol. Chem., 1994, 269:26669-76.) In vitro studies using iNOS inhibitors, s-methylisothiourea and aminoguanidine, have demonstrated inhibition of nitric oxide production and induction of apoptosis mediated by caspase-1/3, and PARP cleavage (Salvucci, O. et al., Cancer Res., 2001, 61:318-26.)

PBIT is an iNOS selective inhibitor that is effective preventing colon and esophageal cancer in rats following dietary administration. However, due to low potency, poor cell permeability and associated systemic toxicity its utility in clinical settings is limited. (Garvey, E. P. et al., J. Biol. Chem., 1994, 269:26669-76; Rao, C. V., Mutat. Res., 2004, 555:107-19; Chen, T. et al., Cancer Res 2004; 64:3714-7.)

Constitutive activation of the MAP (Ras/Raf/Mek/Erk) kinase pathway through Ras mutations in 10-15% and B-Raf mutation in ~60% of melanomas is a second important signaling cascade deregulated in cancers, including melanomas (Madhunapantula, S. V. et al., Cancer Res., 2008, 68:5-8.) Activating B-Raf mutations are acquired, somatic, post-zygotic events and are not inherited in families (Lang J. et al., Hum. Mutat., 2003, 21:327-30.) Among different B-Raf mutations, a single-base missense substitution (T to A at nucleotide 1799) that changes valine to glutamic acid at codon 600 (V600E) in exon 15 is prevalent in ~90% of melanoma tumors with mutation of B-Raf (Davies, H. et al., Nature, 2002, 417:949-54). $^{V600E}$B-Raf protein leads to kinase activity 10.7 times higher than occurs in normal cells and causes hyperactivity of the MAP kinase pathway (Davies, H. et al. Nature, 2002, 417:949-54).

Treatment of cells with PBIT to inhibit iNOS increases MAP kinase pathway activity leading to higher levels of active phosphorylated Erk1/2 and increased expression of downstream iNOS (Ellerhorst, J. A. et al., Oncogene, 2006, 25:3956-62; Tunctan B, et al., Pharmacol. Res., 2007, 56:56-64). Abnormally high activation of the MAP kinase pathway can inhibit cellular growth in a wide variety of normal and cancer cells by promoting cellular senescence, including melanomas (Michaloglou, C. et al., Nature, 2005, 436:720-4; and Dhomen, N. et al., Cancer Cell, 2009, 2009, 15, 294-303.). Recent evidence suggests that constitutively active $^{V600E}$B-Raf initially promotes nevi development during melanoma tumor progression that results in high, intense activation of the MAP kinase pathway is inhibitory and that Akt3 activity is required to phosphorylate B-Raf in order to reduce its and the MAP kinase pathway activity to levels promoting rather than inhibiting proliferation (Cheung, M., et al., Cancer Res., 2008, 68:3429-3439).

Compositions and methods are required to inhibit abnormal cell survival and proliferation. In particular, compositions and methods are required to modulate signaling molecules Akt, iNOS and/or MAP kinase, and reduce survival and proliferation of abnormal cells such as cancer cells.

SUMMARY OF THE INVENTION

Compositions and methods are provided according to embodiments of the present invention which inhibit iNOS, inhibit the Akt3 signaling cascade and/or activate MAP kinase pathways. These properties lead to decreased cell proliferation and increased apoptosis of cancer cells, including melanoma cells. Compositions and methods are provided according to embodiments of the present invention which inhibit cancer cell proliferation by blocking cultured cells in the G2/M phase of the cell cycle and decreasing cyclin D1 expression with corresponding increases in p21 and p27 levels. Compositions and methods are provided according to embodiments of the present invention which promote apoptosis in cancer cells through inhibition of Akt3 signaling leading to increased cleaved caspase-3n and PARP.

Broadly described, compositions are provided according to embodiments of the present invention having the structural formula: R2-R—$(CH_2)_n$—X—C($=$NH)—$NH_2$, where R is phenyl, where R2 is $(CH_2)_n$—X—C($=$NH)—$NH_2$ or R2 is H, where X is S or Se, where each n is independently 2, 3, 4, 5, 6, 7, or 8.

In particular embodiments, the compound having the structural formula R2-R—$(CH_2)_n$—X—C($=$NH)—$NH_2$, where R2 is $(CH_2)_n$—X—C($=$NH)—$NH_2$, where each X is S, and where each n is 2 is excluded.

In particular embodiments, the compound having the structural formula R2-R—$(CH_2)_n$—X—C($=$NH)—$NH_2$, where R2 is H, where X is S, and where n is 2 or 3 is excluded.

In particular embodiments, compositions are provided according to embodiments of the present invention having the structural formula I: R2-R—R1, where R is phenyl, where R1 is $(CH_2)_n$—Se—C($=$NH)—$NH_2$, where R2 is $(CH_2)_n$—Se—C($=$NH)—$NH_2$ or R2 is H, where each n is independently 2, 3, 4, 5, 6, 7, or 8.

Pharmaceutical compositions are provided according to embodiments of the present invention including the composition having the structural formula I, II, III, IV or V.

Pharmaceutical compositions are provided according to embodiments of the present invention which include an inventive composition having the structural formula I, II, III, IV or V; and a pharmaceutically acceptable carrier. Optionally, the pharmaceutically acceptable carrier is a particulate carrier. In a further option, the pharmaceutical composition is formulated for topical application.

Methods of treating a subject are provided according to the present invention which include administering an effective amount of a composition having the structural formula I, II, III, IV or V to a subject in need thereof.

An inventive composition having the structural formula I, II, III, IV or V is optionally conjugated to glutathione, cysteine or N-acetylcysteine to produce a glutathione conjugate; a cysteine conjugate; or an N-acetylcysteine conjugate for administration to a subject in need thereof.

In embodiments of methods including administration of an inventive composition to a subject, the subject is human.

In further embodiments, the subject has or is at risk of having cancer. In certain embodiments, the subject has cancer or is at risk for cancer characterized by dysregulation of Akt1, Akt2 and/or Akt3; iNOS dysregulation; and/or MAP kinase dysregulation. In further embodiments, the cancer is a melanoma.

Methods of treating a subject are provided according to embodiments of the present invention which include administering a therapeutically effective amount of an inventive composition having the structural formula I, II, III, IV or V wherein the subject has a condition characterized by Akt dysregulation, such as cancer, pre-neoplastic hyperproliferation, cancer in-situ, neoplasms, metastasis, tumor or benign growth. In certain embodiments of methods of treatment of a subject, contacting cells characterized by Akt dysregulation with a therapeutic amount of an inventive composition having the structural formula I, II, III, IV or V decreases a component of an Akt signaling pathway selected from the group consisting of an Akt1 signaling pathway; an Akt2 signaling pathway; an Akt3 signaling pathway; and a combination thereof. For example, contacting the cell with a composition having the structural formula I, II, III, IV or V decreases a component of an Akt signaling pathway selected from pAkt1, pAkt2, pAk3, pPRAS40 and a combination thereof. In embodiments of described methods, treatment of a subject with a therapeutically effective amount of the composition having the structural formula I, II, III, IV or V is substantially without toxic effect on cells in which Akt is not dysregulated.

Methods of treating a subject are provided according to embodiments of the present invention which include administering a therapeutically effective amount of an inventive composition having the structural formula I, II, III, IV or V wherein the subject has a condition characterized by iNOS dysregulation, such as cancer, pre-neoplastic hyperproliferation, cancer in-situ, neoplasms, metastasis, tumor or benign growth. In certain embodiments of methods of treatment of a subject, contacting cells characterized by iNOS dysregulation with a therapeutic amount of an inventive composition having the structural formula I, II, III, IV or V decreases a component of an iNOS signaling pathway. In embodiments of described methods, treatment of a subject with a therapeutically effective amount of the composition having the structural formula I, II, III, IV or V is substantially without toxic effect on cells in which iNOS is not dysregulated.

Methods of treating a subject are provided according to embodiments of the present invention which include administering a therapeutically effective amount of an inventive composition having the structural formula I, II, III, IV or V wherein the subject has a condition characterized by MAP kinase dysregulation, such as cancer, pre-neoplastic hyperproliferation, cancer in-situ, neoplasms, metastasis, tumor or benign growth. In certain embodiments of methods of treatment of a subject, contacting cells characterized by MAP kinase dysregulation with a therapeutic amount of an inventive composition having the structural formula I, H, III, IV or V decreases a component of an MAP kinase signaling pathway. In embodiments of described methods, treatment of a subject with a therapeutically effective amount of the composition having the structural formula I, II, III, IV or V is substantially without toxic effect on cells in which MAP kinase is not dysregulated.

Methods of treating a subject are provided according to embodiments of the present invention which include administering a therapeutically effective amount of an inventive composition having the structural formula I, II, III, IV or V wherein the subject has a condition characterized by Akt dysregulation, such as cancer, pre-neoplastic hyperproliferation, cancer in-situ, neoplasms, metastasis, tumor or benign growth.

Methods according to embodiments of the present invention include administering a therapeutically effective amount of an inventive composition having the structural formula I, II, III, IV or V to a subject wherein the administration detectably increases apoptosis and/or decreases proliferation of cells of the cancer, pre-neoplastic hyperproliferation, cancer in-situ, neoplasms, metastasis, tumor or benign growth.

Optionally, an inventive composition having the structural formula I, II, III, IV or V according to embodiments of the present invention is formulated for topical application, for instance to treat cancer, pre-neoplastic hyperproliferation, cancer in-situ, neoplasms, metastasis, tumor or benign growth of the skin.

Optionally, methods of the present invention additionally include administration of an adjunct anti-cancer treatment.

A method of modulating Akt dysregulation in a cell is provided according to embodiments of the present invention which includes contacting the cell with an effective amount of an inventive composition having the structural formula I, II, III, IV or V. In certain embodiments of methods of modulating Akt dysregulation, contacting the cell with an inventive composition having the structural formula I, II, III, IV or V decreases a component of an Akt signaling pathway selected from the group consisting of: an Akt1 signaling pathway; an Akt2 signaling pathway; an Akt3 signaling pathway; and a combination thereof. For example, contacting the cell with an inventive composition having the structural formula I, II, III, IV or V decreases a component of an Akt signaling pathway selected from pAkt1, pAkt2, pAk3, pPRAS40 and a combination thereof.

A method of modulating Akt dysregulation in a cell is provided according to embodiments of the present invention which includes contacting the cell with an effective amount of an inventive composition having the structural formula I, II, III, IV or V.

A method of modulating Akt dysregulation in a cell is provided according to embodiments of the present invention which includes contacting the cell with an effective amount of an inventive composition having the structural formula I, II, III, IV or V. In certain embodiments of methods of modulating Akt dysregulation, contacting the cell with an inventive composition having the structural formula I, II, III, IV or V decreases a component of an Akt signaling pathway selected from the group consisting of: an Akt1 signaling pathway; an Akt2 signaling pathway; an Akt3 signaling pathway; and a combination thereof. For example, contacting the cell with an inventive composition having the structural formula I, II, III, IV or V decreases a component of an Akt signaling pathway selected from pAkt1, pAkt2, pAk3, pPRAS40 and a combination thereof.

BRIEF DESCRIPTION OF THE DRAWINGS

FIG. 1A is a drawing illustrating chemical structures of particular compositions according to embodiments of the present invention;

FIG. 1B shows two graphs illustrating the effects of various concentrations of PBIT and PBISe on viability of Caco-2 colon adenocarcinoma cells;

FIG. 1C shows two graphs illustrating the effects of various concentrations of PBIT and PBISe on nitrate+nitrite amounts in Caco-2 colon adenocarcinoma cells;

FIG. 2A is a graph showing the effects of various concentrations of PBIT and PBISe on viability of UACC 903 melanoma cells;

FIG. 2B is a table of PBISe $IC_{50}$ values in melanoma cells and normal human fibroblasts;

FIG. 2C is a graph illustrating the effects of various concentrations of PBIT and PBISe on proliferation in UACC 903 melanoma cells;

FIG. 2D is a graph illustrating the effects of various concentrations of PBIT and PBISe on apoptosis in UACC 903 melanoma cells;

FIG. 3A is a graph illustrating the effects of various concentrations of PBIT and PBISe on cell cycle (sub-G0-G1 population) in UACC 903 melanoma cells;

FIG. 3B is a graph illustrating the effects of various concentrations of PBIT and PBISe on cell cycle (G2-M population) in UACC 903 melanoma cells;

FIG. 3C is a table illustrating the effects of various concentrations of PBIT and PBISe on cell cycle in UACC 903 melanoma cells;

FIG. 4A is a reproduction of an image of an immunoblot illustrating changes in various proteins involved in Akt3 signaling following treatment of cells with PBIT or PBISe;

FIG. 5B shows two graphs illustrating the effects of PBIT and PBISe on tumor volume and body weight in mice;

FIG. 6 is a reproduction of an image of an immunoblot illustrating changes in various proteins involved in Akt3 signaling following treatment of Caco-2 cells with PBIT or PBISe;

FIG. 7A is a reproduction of images of sections stained with hematoxylin and eosin showing cell morphology and overall structural integrity of PBISe treated and control sections;

FIG. 7B shows a graph of the area occupied by tumor nodules in reconstructed skin containing WM35 GFP cells after topical treatment with PBISe or PBIT, along with representative fluorescent micrographs;

FIG. 7C shows a graph of the area occupied by tumor nodules in reconstructed skin containing UACC 903 GFP cells after topical treatment with PBISe or PBIT, along with representative fluorescent micrographs;

FIG. 8A shows graphs indicating that there is a significant (<P<0.05) 50% decrease in tumor volume between PBISe treated and vehicle acetone treated and PBIT control treated mice;

FIG. 8B is a graph showing no detectable differences of body weight in mice treated with PBIT, PBISe or vehicle; and FIG. 8C is a graph showing no significant differences in serum enzyme and metabolite levels in mice treated with PBIT, PBISe or vehicle.

DETAILED DESCRIPTION OF THE INVENTION

Figure 4B:
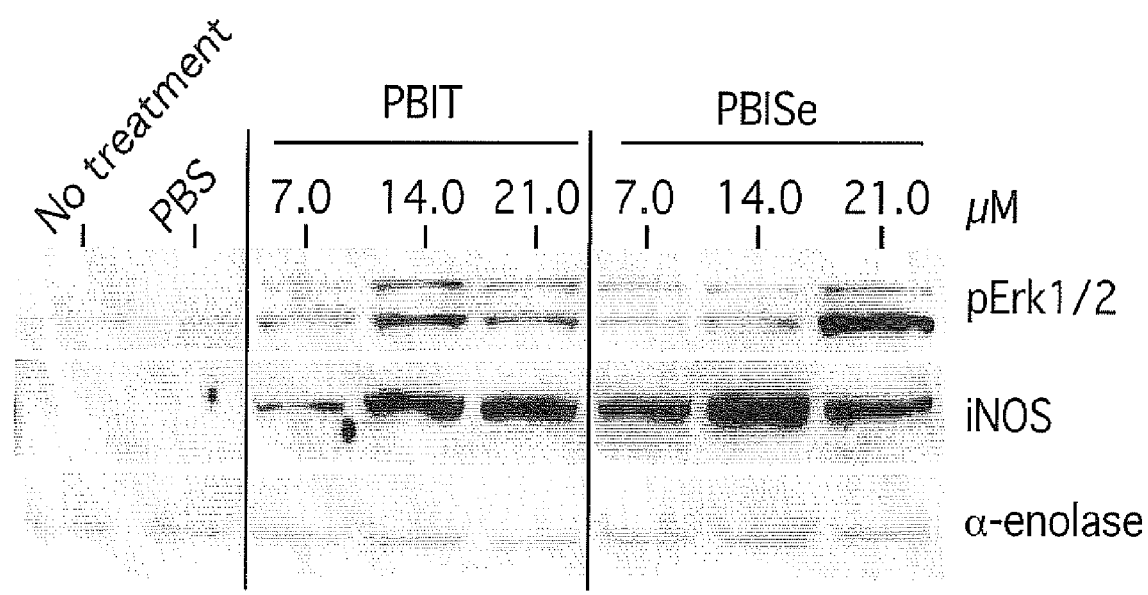
FIG. 4B is a reproduction of an image of an immunoblot illustrating changes in pErk1/2 and iNOS proteins following treatment of cells with PBIT or PBISe.

Anti-cancer compositions and methods are provided according to embodiments of the present invention. In certain embodiments, the present invention relates to inventive compositions, methods for treatment and/or prevention of pathological conditions in a subject using one or more inventive compositions having the structural formula I, II, III, IV or V.

Broadly described, compositions are provided according to embodiments of the present invention having the structural formula: R2-R—$(CH_2)_n$—X—C(=NH)—$NH_2$, where R is phenyl, where R2 is $(CH_2)_n$—X—C(=NH)—$NH_2$ or R2 is H, where X is S or Se, where each n is independently 2, 3, 4, 5, 6, 7, or 8, along with methods of use of the compositions.

In particular embodiments, the compound having the structural formula R2-R—$(CH_2)_n$—X—C(=NH)—$NH_2$, where R2 is $(CH_2)_n$—X—C(=NH)—$NH_2$, where each X is S, and where each n is 2 is excluded.

In particular embodiments, the compound having the structural formula R2-R—(CH$_2$)$_n$—X—C(=NH)—NH$_2$, where R2 is H, where X is S, and where n is 2 or 3 is excluded.

In particular embodiments, compositions are provided according to embodiments of the present invention having the structural formula I: R2-R—R1, where R is phenyl, where R1 is (CH$_2$)$_n$—Se—C(=NH)—NH$_2$, where R2 is (CH$_2$)$_n$—Se—C(=NH)NH$_2$ or R2 is H, where each n is independently 2, 3, 4, 5, 6, 7, or 8.

R1 and R2 can have para-, meta- or ortho-positions with respect to each other. R is optionally further substituted by one or more of the following: F, Cl, Br, a lower alkyl group, a lower alkoxy group or fluorinated lower alkyl group, such as CF$_3$.

The term "lower alkoxy" as used herein refers to a straight chain or branched hydrocarbon group containing from 1-4 carbon atoms which is appended to the parent molecular moiety through an oxygen atom. Illustrative examples of lower alkyl groups are methoxy, ethoxy, propoxy, 2-propoxy, butoxy and tert-butoxy.

The term "lower alkyl" as used herein refers to a straight chain or branched hydrocarbon group containing from 1-4 carbon atoms. Illustrative examples of lower alkyl groups are methyl, ethyl, iso-propyl, n-propyl, n-butyl, iso-butyl, sec-butyl and tert-butyl.

In particular embodiments, compositions of the present invention have the structural formula II:

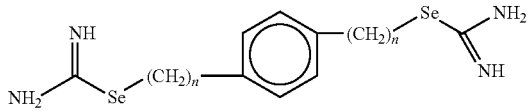

where each n is independently 2, 3, 4, 5, 6, 7 or 8.

In particular embodiments, an inventive composition according to the present invention has the structural formula III:

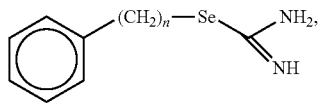

where n is 2, 3, 4, 5, 6, 7 or 8.

In particular embodiments, an inventive composition according to the present invention has the structural formula IV:

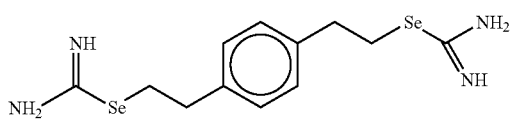

In particular embodiments, an inventive composition according to the present invention has the structural formula V:

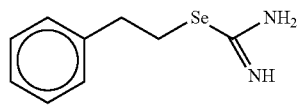

In each of compositions having structural formulas II, III, IV and V the phenyl is optionally further substituted by one or more of the following: F, Cl, Br, a lower alkyl group, a lower alkoxy group or fluorinated lower alkyl group, such as CF$_3$.

Compositions including mixtures of two or more inventive compositions having structural formula I are also specifically contemplated and are considered to be within the scope of the present invention.

Conjugate Compositions

A compound of the present invention having structural formula I is conjugated to one or more property-enhancing moieties according to embodiments of the present invention for modification of one or more characteristics of the compound. The present invention provides conjugate compositions, in order to reduce toxicity, increase solubility and/or increase bioavailability in particular embodiments of the present invention. Methods of synthesis of such conjugates are also provided by embodiments of the presently described invention.

For example, in particular embodiments, a compound of the present invention having structural formula I is conjugated to a water solubility-enhancing moiety, to yield a conjugate which is more water soluble than the compound. Thus, in particular embodiments, compositions of the present invention having structural formula I, II, III, IV or V are conjugated to glutathione (GSH), cysteine (Cys) or N-acetylcysteine (NAC) to yield the corresponding GSH-, Cys-, or NAC-conjugate such that the conjugate has increased water solubility compared to the parent composition having structural formula I, II, III, IV or V.

NAC-conjugates are made by reacting corresponding inventive composition with N-acetylcysteine in aqueous ethanol (50%) at room temperature under nitrogen atmosphere. GSH or cysteine conjugates of inventive compositions having structural formula I are synthesized following a similar procedure.

Compositions according to embodiments of the present invention prevent and inhibit cancer cell multiplication and tumor development and are considered useful as chemotherapeutic and chemopreventive agents. In addition, selenium-containing compositions having structural formula I according to embodiments of the present invention induce cell death in cancer cells more effectively than corresponding sulfur-containing compositions or derivatives thereof.

Methods and compositions are provided according to the present invention for treating cancer. Particular cancers treated using methods and compositions described herein are characterized by abnormal cell proliferation including, but not limited to, pre-neoplastic hyperproliferation, cancer in-situ, neoplasms and metastasis. Methods and compositions of the present invention can be used for prophylaxis as well as amelioration of signs and/or symptoms of cancer.

A therapeutically effective amount of a composition of the present invention is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to a composition of the present invention, a therapeutically effective amount of a composition of the present invention is effective to ameliorate or prevent one or more signs and/or symptoms of the condition. For example, a therapeutically effective amount of a composition of the present invention is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to a composition of the present invention.

In particular embodiments, cancers treated using methods and compositions of the present invention are characterized by Akt dysregulation, iNOS dysregulation and/or MAP kinase dysregulation.

Akt, a serine/threonine protein kinase also known as protein kinase B, has a stimulatory effect on cell cycle progression, cell proliferation and inhibition of apoptosis. Akt proteins, nucleic acids and signaling pathway components are described, for instance, see Testa, J. R. et al., PNAS, 98:10983-10985; Fayard, E. et al., J. Cell Sci., 118:5675-5678, 2005; Cheng, J. and S, Nicosia, (2001) AKT signal transduction pathway in oncogenesis, in Encyclopedic Reference of Cancer, D. Schwab, Editor. 2001, Springer: Berlin, Germany, p. 35-7; Datta, S. R., et al. (1999) Cellular survival: a play in three Akts. Genes Dev, 13(22): 2905-27; Fayard, E. et al. (2005) J Cell Sci, 118 (Pt 24: 5675-8; Mirza, A. M., Fayard, E. et al. (2000) 2000. 11 (6: 279-92; Nicholson, K. M. and N. G. Anderson, (2002) Cell Signal, 2002, 14(5): p. 381-95; Paez, J. and W. Sellers, (2003) P13K/PTEN/Akt Pathway: A Critical Mediator of Oncogenic Signaling, in Signal Transduction in Cancer, D. Frank, Editor. 2003, Kluwer Academic Publishers: Netherlands; and Testa, J. R.; P. N. Tsichlis, (2005) Oncogene, 24(50): 7391-3 and other references listed herein.

Akt family members, Akt1, Akt2 and Akt3, are activated by phosphorylation, membrane translocation, increases in gene copy number and/or loss of a negative regulatory phosphatase, PTEN. Increased activation of Akt, including increased levels of Akt and/or increased levels of phosphorylated Akt is an indicator of Akt dysregulation associated with proliferation and cell survival in pathogenic conditions, such as cancer.

Akt3 is active in ~70% of melanomas. While all three Akt isoforms are expressed in melanocytes and melanoma cells, Akt3 is the predominantly active family member. Dysregulated Akt3 activity in melanoma cells reduces cellular apoptosis mediated through caspase-3, thereby promoting melanoma tumor development.

Akt dysregulation is determined, for instance, by measurement of Akt gene copy number, Akt protein or RNA levels and/or levels of phosphorylated Akt, in cells known or suspected to be dysplasic, pre-cancerous, cancerous, metastatic or otherwise characterized by abnormal cell proliferation compared to normal cells. Assays for Akt dysregulation include, but are not limited to immunoassays and nucleic acid assays.

Methods of treating a subject are provided according to embodiments of the present invention which include administering a therapeutically effective amount of an inventive composition having structural formula I, II, III, IV or V wherein the subject has a condition characterized by Akt dysregulation, such as cancer, pre-neoplastic hyperproliferation, cancer in-situ, neoplasms, metastasis, tumor or benign growth. In certain embodiments of methods of treatment of a subject, contacting cells characterized by Akt dysregulation with a therapeutic amount of an inventive composition having structural formula I, II, III, IV or V decreases a component of an Akt signaling pathway selected from the group consisting of: an Akt1 signaling pathway; an Akt2 signaling pathway; an Akt3 signaling pathway; and a combination thereof. For example, contacting the cell with an inventive composition having structural formula I, II, III, IV or V decreases a component of an Akt signaling pathway selected from pAkt1, pAkt2, pAk3, pPRAS40 and a combination thereof. In embodiments of described methods, treatment of a subject with a therapeutically effective amount an inventive composition having structural formula I, II, III, IV or V is substantially without toxic effect on cells in which Akt is not dysregulated.

Methods of treating a subject are provided according to embodiments of the present invention which include administering a therapeutically effective amount of a composition having the structural formula I, II, III, IV or V and wherein the subject has a condition characterized by Akt dysregulation, such as cancer, pre-neoplastic hyperproliferation, cancer in-situ, neoplasms, metastasis, tumor or benign growth.

Methods of treating a subject are provided according to embodiments of the present invention which include administering a therapeutically effective amount of a composition having structural formula I, II, III, IV or V to a subject in need thereof, wherein the subject has a condition characterized by Akt dysregulation, such as cancer, pre-neoplastic hyperproliferation, cancer in-situ, neoplasms, metastasis, tumor or benign growth.

A method of treating a subject is provided according to embodiments of the present invention which includes administering to a subject in need thereof a therapeutically effective amount of one or more compounds having the structural formula I, II, III, IV or V.

In embodiments of the present invention, a method of treating a subject includes administering an effective amount of a composition having the structural formula II:

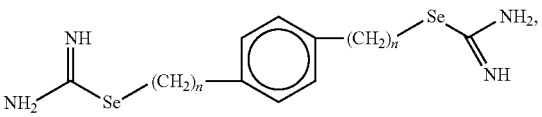

where each n is independently 2, 3, 4, 5, 6, 7 or 8.

In embodiments of the present invention, a method of treating a subject includes administering an effective amount of a composition having the structural formula III:

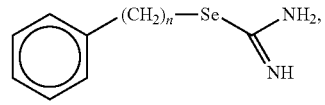

where n is 2, 3, 4, 5, 6, 7 or 8.

In embodiments of the present invention, a method of treating a subject, includes administering an effective amount of a composition having the structural formula IV:

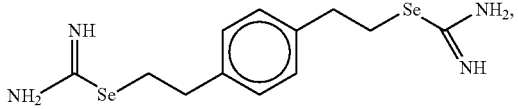

In embodiments of the present invention, a method of treating a subject, includes administering an effective amount of a composition having the structural formula V:

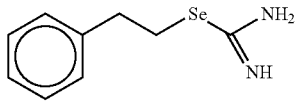

In each of compositions having structural formulas I, II, III, IV and V the phenyl is optionally further substituted by one or more of the following: F, Cl, Br, a lower alkyl group, a lower alkoxy group or fluorinated lower alkyl group, such as $CF_3$.

Optionally, an administered composition having structural formula I, II, III, IV or V is a glutathione conjugate; a cysteine conjugate; or an N-acetylcysteine conjugate.

Optionally, an administered composition having structural formula I, II, III, IV or V is a pharmaceutically acceptable salt, ester, amide or solvate of a composition described herein.

A "pharmaceutically acceptable" salt, ester, amide or solvate is suitable for use in a subject without undue toxicity or irritation to the subject and is effective for their intended use.

Pharmaceutically acceptable salts include pharmaceutically acceptable acid addition salts and base addition salts. Pharmaceutically acceptable salts are well-known in the art, such as those detailed in S. M. Berge et al., J. Pharm. Sci., 66:1-19, 1977. Exemplary pharmaceutically acceptable salts are those suitable for use in a subject without undue toxicity or irritation to the subject and which are effective for their intended use which are formed with inorganic acids such as hydrochloric acid, hydrobromic acid, hydroiodic acid, nitric acid, phosphoric acid, sulfuric acid and sulfamic acid; organic acids such as acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid; inorganic bases such as ammonia, hydroxide, carbonate, and bicarbonate of ammonium; organic bases such as primary, secondary, tertiary and quaternary amine compounds ammonium, arginine, betaine, choline, caffeine, diolamine, diethylamine, diethanolamine, 2-dimethylaminoethanol, 2-diethylaminoethanol, dicyclohexylamine, dicyclohexylamine, dibenzylamine, N,N-dibenzylphenethylamine, 1-ephenamine, N,N'-dibenzylethylenediamine, ethanolamine, ethylamine, ethylenediamine, glucosamine, histidine, hydrabamine, isopropylamine, 1h-imidazole, lysine, methylamine, N-ethylpiperidine, N-methylpiperidine, N-methylmorpholine, N,N-dimethylaniline, piperazine, trolamine, methylglucamine, purines, piperidine, pyridine, theobromine, tetramethylammonium compounds, tetraethylammonium compounds, trimethylamine, triethylamine, tripropylamine and tributylamine and metal cations such as aluminum, calcium, copper, iron, lithium, magnesium, manganese, potassium, sodium, and zinc.

Pharmaceutically acceptable solvates illustratively include hydrates, ethanolates, methanolates.

Exemplary pharmaceutically acceptable amides include amides derived from ammonia, primary C1-C6 alkyl amines and secondary C1-C6 dialkyl amines including those in the form of a 5- or 6-member nitrogen-containing heterocycle.

Compositions having structural formula I, II, III, IV and V are provided according to embodiments of the present invention which inhibit tumor growth by inhibiting an Akt signaling cascade, particularly an Akt3 signaling cascade, in cells characterized by Akt dysregulation in certain embodiments.

Methods including administration of one or more compositions having structural formula I, II, III, IV and V to a subject in need thereof are provided according to particular embodiments of the present invention which have utility, for example, in inhibiting the Akt signaling cascade and inhibiting cancer cells.

Inhibitors of the Akt signaling cascade according to embodiments of the present invention have utility in treatment of subject having cancer or at risk of having cancer in which Akt deregulation occurs, such as in melanoma and other cancers including, but not limited to, cancers of the prostate, breast, brain, ovary, lung, colon, connective tissues (sarcomas) and soft tissue.

Methods of modulating an Akt protein, such as an Akt1, Akt2 and/or an Akt3 protein, in a cell are provided according to embodiments of the present invention which include contacting the cell with an effective amount of a composition having structural formula I, II, III, IV or V.

iNOS

Inducible nitric oxide synthase (iNOS) is a calcium independent, cytokine inducible enzyme. Among the three forms of NOS, only iNOS has been implicated in the origin of several cancers including melanoma (Fitzpatrick, B., et al., Nitric Oxide, 2008, 19, 217-224; Grimm, E. A., et al., Nitric Oxide, 2008, 19, 133-137; Rao, C. V., Mutation Res. 2004, 555, 107-119; Cobbs, C. S. et al., Cancer Res., 1995, 55, 727-730). The catalytic product of iNOS nitric oxide, NO, has been shown to contribute to the pathogenesis of a variety of cancers (Uffort, D. G. et al., J. Invest. Dermatol., 2009, 129, 148-154). Nitric oxide protects tumor cells from apoptosis and thereby increases cell survival. Furthermore, inhibition of iNOS expression or activity using specific siRNAs or small molecule inhibitors has been shown to decrease tumor cell proliferation (Salvucci, O. et al., Cancer Res. 2001, 61, 318-326; Madhunapantula, S. V. et al., Mol. Cancer. Ther. 2008, 7, 1297-1308).

Expression and activity of iNOS is regulated at transcriptional and translational level by growth factors, stimulating agents such as TNFα, IFNγ and interleukins. Recently NF-κB has been shown to control the expression of iNOS induced by MAPkinases in melanoma (Uffort, D. G. et al., J. Invest. Dermatol., 2009, 129, 148-154).

iNOS expression in cell lines and tumor samples can be monitored by immunohistochemical staining, Western blotting, and by measuring the mRNA levels by PCR. The activity of iNOS can be determined by colorimetric assays measuring the amount of NO released from a given sample.

MAP Kinases

MAP kinase signaling pathway relays extracellular signals from cell surface to the cytosol and nucleus via ordered series of consecutive phosphorylation and dephosphorylation events (Madhunapantula, S. V., et al., Cancer Res. 2008. 68, 5-8). Oncogenic role of Raf kinases has been reported in several cancers including melanoma (Davies, H., et al., Nature, 2002, 417, 949-954). Among the three isoforms (A-Raf, B-Raf and C-Raf) of Raf kinases, B-Raf has been demonstrated to undergo mutational changes and is prime cause of human cancers. In melanomas, $^{V600E}$B-Raf mutation has been reported in 60-70% of melanomas. Furthermore, targeting B-Raf using siRNA or pharmacological agents such as sorafenib decrease melanoma tumor development and metastasis in vitro and in vivo by inhibiting proliferation and vascular development (Sharma, A., et al., Cancer Res. 2005, 65, 2412-2421; Sharma, A., et al., Cancer Res., 2006, 66, 8200-8209).

Recent studies have found that B-Raf, apart from regulating proliferation, also regulate cell senescence (Cheung, M et al., Cancer Res. 2008, 68, 3429-3439; Dhomen, N. et al., Cancer Cell, 2009, 2009, 15, 294-303; Houben, R., et al., J Invest. Dermatol. 2009, 129, 406-414). Additionally targeting B-Raf in combination with Akt3 inhibit melanoma tumor development more effectively than targeting either proteins alone (Tran, M et al., Cancer Res. 2008, 68, 7638-7649; Cheung, M et al., Cancer Res. 2008, 68, 3429-3439). Furthermore, B-Raf has been shown to cooperate with PTEN loss to promote melanoma development in mice (Dankort, D., et al., Nature Gen. 2009, 1-9). Hence, it is now widely accepted that whereas optimal B-Raf activity promote cell growth and division unusual activity levels trigger cellular senescence thereby inhibit tumor development.

MAPkinase activity can be monitored by measuring the kinase activity using suitable substrate proteins, immunohistochemical staining procedures looking at the pErk1/2 levels, in vitro and in vivo proliferation assays measuring BrdU incorporation or ki67 staining, and by Western blotting.

Pharmaceutical compositions including a composition having structural formula I, II, III, IV or V of the present invention are also provided according to embodiments of the present invention.

In each of pharmaceutical compositions having structural formulas I, II, III, IV and V, the phenyl is optionally further substituted by one or more of the following: F, Cl, Br, a lower alkyl group, a lower alkoxy group or fluorinated lower alkyl group, such as $CF_3$.

A pharmaceutical composition includes a composition having structural formula I, III, IV or V of the present invention and a pharmaceutically acceptable carrier in particular embodiments of the present invention. The term "pharmaceutically acceptable carrier" refers to a carrier which is substantially non-toxic to a subject to which the composition is administered and which is substantially chemically inert with respect to a composition having structural formula I, II, III, IV or V of the present invention.

A pharmaceutical composition according to the invention generally includes about 0.1-99% of a composition having structural formula I, II, III, IV or V. Combinations of compositions having structural formula I, II, III, IV or V in a pharmaceutical composition are also considered within the scope of the present invention.

Optionally, a method of treating a subject having cancer or at risk of having cancer further includes an adjunct anti-cancer treatment. An adjunct anti-cancer treatment can be administration of an anti-cancer agent.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, fluorocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazafurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An adjunct anti-cancer treatment can be a radiation treatment of a subject or an affected area of a subject's body.

Pharmaceutical compositions suitable for delivery to a subject may be prepared in various forms illustratively including physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, selenium-containing compound of the present invention is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to an inventive conjugate, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

In particular embodiments, compositions of the present invention are formulated for topical application. In further particular embodiments, compositions of the present invention are formulated for topical application and are characterized by less than 10% absorption of an active ingredient in the composition into the system of an individual treated topically. In still further particular embodiments, compositions of the present invention are formulated for topical application and are characterized by less than 9%, 8%, 7%, 6%, 5%, 4%, 3%, 2%, 1% absorption of an active ingredient in the composition into the system of an individual treated topically. Absorption into the system of an individual can be measured by any of various methods, particularly assay for the active ingredient, a metabolite and/or a breakdown product of the active ingredient in a sample obtained from an individual treated with the topical formulation. For example, a blood, plasma or serum sample can be assayed for presence of the active ingredient, a metabolite of the active ingredient and/or a breakdown product of the active ingredient.

A topical formulation can be an ointment, lotion, cream or gel in particular embodiments. Topical dosage forms such as ointment, lotion, cream or gel bases are described in Remington: The Science and Practice of Pharmacy, 21$^{st}$ Ed., Lippincott Williams & Wilkins, 2006, p. 880-882 and p. 886-888; and in Allen, L. V. et al., Ansel's Pharmaceutical Dosage Forms and Drug Delivery Systems, 8$^{th}$ Ed., Lippincott Williams & Wilkins, 2005, p. 277-297.

Pharmaceutically acceptable carriers and formulation of pharmaceutical compositions are known in the art, illustratively including, but not limited to, as described in Remington: The Science and Practice of Pharmacy, 21$^{st}$ Ed., Lippincott, Williams & Philadelphia, Pa., 2006; and Allen, L. V. et al., Ansel's Pharmaceutical Dosage Forms and Drug Delivery Systems, 8$^{th}$ Ed., Lippincott, Williams & Wilkins, Philadelphia, Pa., 2005.

The term subject refers to an individual in need of treatment for a pathological condition, particularly cancer, and generally includes mammals and birds, such as, but not limited to, humans, other primates, cats, dogs, cows, horses, rodents, pigs, sheep, goats and poultry.

A pharmaceutical composition according to the present invention is suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

An inventive composition may be administered acutely or chronically. For example, a composition as described herein may be administered as a unitary dose or in multiple doses over a relatively limited period of time, such as seconds—hours. In a further embodiment, administration may include multiple doses administered over a period of days—years, such as for chronic treatment of cancer.

With regard to administration of a particular inventive composition to a mammalian subject, particular exemplary effective dosage ranges without significant systemic toxicity are described in terms of amounts of selenium administered via administration of the inventive composition. Thus, for example, when delivered by a parenteral route, such as intraperitoneal or intravenous, an exemplary therapeutically effective dosage of an inventive composition is in the range of about 1-4 ppm selenium, administered three times per week. It is noted that the dose range "about 1-4 ppm selenium" refers to a dose of "about 1 mg/kg-10 mg/kg of selenium," depending on the particular compound administered. For example, in particular embodiments PBISe or PEISe is administered intraperitoneally (i.p.) at a dose of 2.5 ppm three times a week. Each dose is equivalent to 8.53 mg of PBISe/kg body weight. Similarly, 2.5 ppm PEISe is equivalent to 9.75 mg/kg body weight.

In a further example, when delivered topically, an exemplary therapeutically effective dosage of a selenium containing compound described herein is in the range of about 0.1-2 ppm selenium, administered daily. In one example, topically administered PBISe is given at a dose of 1.5 ppm selenium (equivalent to 5.12 mg/kg body weight) every day.

In a further example, when delivered orally, an exemplary therapeutically effective dosage of a selenium containing compound described herein is in the range of about 1-15 ppm selenium. In a particular example, an oral dose in the range of 1-15 ppm of selenium equivalent to 3.412 mg/kg-51.18 mg/kg body weight of PBISe is a therapeutically effective dose.

A therapeutically effective amount of a pharmaceutical composition according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

Advantageously, anti-cancer compounds according to embodiments of the present invention are formulated to achieve lipid-solubility and/or aqueous-solubility.

In particular embodiments, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 mm-10 microns. In particular embodiments, a particulate carrier is formulated such that particles have an average particle size in the range of about 1 nm 100 nm.

Embodiments of inventive compositions and methods are illustrated in the following examples. These examples are provided for illustrative purposes and are not considered limitations on the scope of inventive compositions and methods.

EXAMPLES

Example 1

Cell lines and culture conditions. Metastatic melanoma cell lines UACC 903 and 1205Lu; lung adenocarcinoma (A549; ATCC No. CCL-185), fibrosarcoma (HT-1080; ATCC No. CCL-121), prostate adenocarcinoma (PC-3; ATCC No. CRL-1435), ovarian adenocarcinoma (NIH:OVCAR-3; ATCC No. HTB-161), normal human fibroblast cells (FF2441) and a breast adenocarcinoma cell line (MDA-MB-231; ATCC No. HTB-26) are grown in DMEM supplemented with 10% FBS. Vertical growth phase (VGP) melanoma cell line WM115 is maintained in Tu2% medium lacking calcium chloride, supplemented with 2% heat treated (56° C. for 30 minutes) FBS and L-glutamine (Mediatech, Handon, Va.) (Stahl, J. M., et al., Cancer Res 2004; 64:7002-10.). Colon adenocarcinoma cell lines (Caco-2; ATCC No. HTB-37., ATCC No. CCL-247., HT-29; ATCC No. HTB-38., SW-480; ATCC No. CCL-228) are grown in Advanced DMEM supplemented with 10% heat inactivated (56° C. for 30 minutes) FBS and 2 mM L-glutamine.

Example 2

Synthesis

Melting points are recorded on a Fisher-Johnson melting point apparatus and are uncorrected. Unless stated otherwise, proton NMR spectra are recorded in $CDCl_3$ using a Bruker 500 MHz instruments. The chemical shifts are reported in ppm downfield from TMS. High-resolution MS are determined on a Finnigan Mat95 instrument at the Penn State University, University Park, Pa. Thin-layer chromatography (TLC) is done on aluminum-supported, pre-coated silica gel plates (EM Industries, Gibbstown, N.J.).

Selenium-containing compounds, namely S,S'-1,4-phenylenebis(1,2-ethanediyl)bis-isoselenourea (PBISe, 2) and s-2-phenylethylisoselenourea hydrobromide (PEISe, 4) are synthesized as described hereinbelow.

PBISe, 2, and iNOS inhibitor PBIT, 1, shown below and in FIG. 1A, are prepared as shown in scheme I, a modification of a method described in Garvey, E. P. et al., J Biol Chem, 269: 26669, 1994).

Scheme 1: Synthesis of PBIT (1) and PBISe (2)

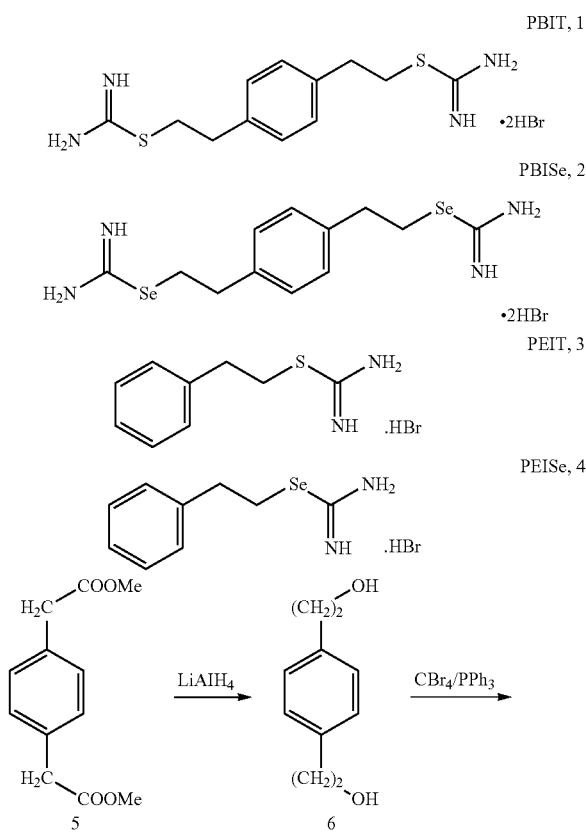

-continued

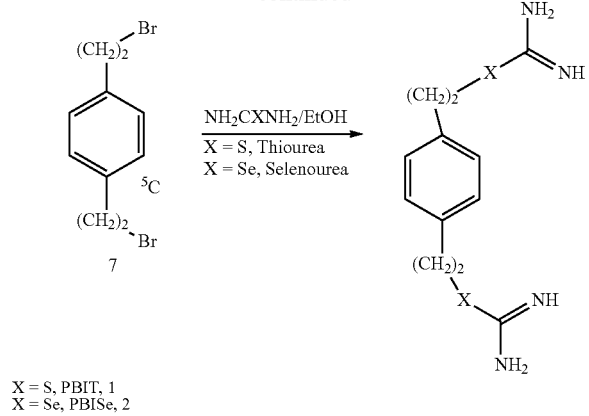

X = S, PBIT, 1
X = Se, PBISe, 2

Methyl ester 5 is prepared as reported in the literature by refluxing 1,4-phenylenediacetic acid with methanol and $H_2SO_4$ in catalytic amount (Whitmore, F. C., et al., J. Am. Chem. Soc. 1938, 60, 2790). Reduction with $LiAlH_4$ in THF yielded dihydrodiol 6 in good yield. The diol 6 is converted to the dibromo derivative 7 by reacting with Carbon tetrabromide and triphenyl phosphine (Garvey, E. P. et al., J Biol Chem, 269: 26669, 1994). Dibromo derivative 7 is reacted with thiourea or selenourea to yield the desired product PBIT, 1 and PBISe, 2 as dihydrobromide salt, respectively.

PEIT, 3 is prepared by following literature method (Garvey, E. P. et al., J Biol Chem, 269: 26669, 1994) and PEISe (4) is prepared in a similar manner by reacting 2-bromoethyl benzene with selenourea to give the desire product PEISe 4 in quantitative yield. Methyl 1,4-phenylenediacetic acid (5), 1,4-phenylene diethanol (6), and 1,4-di(2-bromoethyl)benzene (7) are prepared as described in Garvey, E. P. et al., J Biol Chem, 269: 26669, 1994. All starting materials and reagents are obtained from Aldrich Chemical Co. (Milwaukee, Wis.) and used without further purification.

Synthesis of s,s'-1,4-phenylene-bis(1,2-ethanediyl) bis-isothiourea dihydrobromide (PBIT, 1)

To a mixture of 1,4-di(2-bromoethyl)benzene (7) (1.0 g, 3.43 mmol) in ethanol (50 mL) is added thiourea (0.52 g, 6.86 mmol). The reaction mixture is heated to reflux for 2 h. After concentration of ethanol (20 mL), the precipitated solid is filtered, washed with hexane, methylene chloride, and dried to yield 1 (1.19 g, 78%) as white powder, mp, 234-236° C. $^{62}$; 1H NMR ($D_2O$): 7.25 (s, 4H, aromatic), 3.37 (t, 4H, Ph-CH2, J=7.2 Hz), 3.00 (t, 4H, C—CH2, J=6.86 Hz); MS m/z 194 (20), 1164 (40), 117 (100).

Synthesis of s,s'-1,4-phenylene-bis(1,2-ethanediyl) bis-isoselenourea dihydrobromide (PBISe, 2)

Compound 2 is prepared in a similar manner as reported for compound 1 by reacting 1,4-di(2-bromoethyl)benzene (7) (1.0 g, 3.43 mmol) with selenourea (0.84 g, 6.86 mmol) to yield 2 (1.75 g, 69%), mp, 247-249° C.; 1H NMR ($D_2O$): 7.25 (s, 4H, aromatic), 3.37 (t, 4H, Ph-CH2, 7.2 Hz), 3.21 (t, 4H, C—CH2, 6.86 Hz); MS m/z 194 (20), 1164 (40), 117 (100); ESI-MS: m/z, calcd: 378.9934 for $C_{12}H_1N_4Se_2$; found: 378.9935.

Synthesis of s-2-phenylethylisoselenourea hydrobromide (PEISe, 4)

Compound 4 is prepared in similar manner as reported above for compound 2 by reacting 2-bromoethyl benzene (1.0 g, 5.4 mmol) with selenourea (0.67 g, 5.4 mmol) to yield 4 (1.26 g, 80%); mp, 140-142° C.; $^1$H-HMR ($D_2O$): 7.29-7.20 (m, 5H, aromatic), 3.02 (t, 2H, J=7.0 Hz, $CH_2$-Ph), 3.48 (t, 2H, J=7.0 Hz, $CH_2$—Se,); EMS (m/z, intensity): 229 (M+, 100), 181 (80), 159 (10), 105 (10).

ESI-MS showed an observed molecular weight close to the calculated mass. For example calculated m/z for PBISe is 378.9934 and the observed m/z is 378.9935.

Example 3

Inhibition of Growth of Colon Adenocarcinoma Cells

In vitro inhibitory efficacy is measured using 3-(4,5-dimethylthiazol-2-yl)-5-(3-carboxymethoxyphenyl)-2-(4-sulfophenyl)-2H-tetrazolium (MTS) assay (Promega, Madison, Wis.). $5×10^3$ Caco-2 colon adenocarcinoma cells per well in 100 μL DMEM containing 10% FBS are grown in a 96-well plate for 24. Cells are treated with either vehicle control, PBS, PBIT (40-120 μM) or PBISe (2.4-10 μM) for 72 h. The percentages of viable cells compared to control PBS treated cells are determined using MTS assay and $IC_{50}$ values calculated using GraphPad Prism version 4.01 (GraphPad software, San Diego, Calif.). An $IC_{50}$ value for each compound is determined by at least three independent experiments and represented with a standard error. FIG. 1B is a graph showing the effect of PBISe and PBIT on colon adenocarcinoma cells. PBISe is significantly more effective having an $IC_{50}$ of 2.4 μM indicating a 25-fold increase in potency compared to PBIT. Thus, PBISe is a more potent inhibitor of colon adenocarcinoma cells than PBIT.

Example 4

Nitrite Estimation

Nitrite content in cell culture media is determined using a nitrate/nitrite colorimetric assay kit (Cayman Chemical Company, Ann Arbor, Mich.) essentially as described in Salvucci, O. et al., Cancer Res 2001; 61:318-26. Caco-2 cells ($1×10^6$) are plated in 60 mm culture dishes in advanced DMEM containing 10% heat treated FBS for 12 hours, growing cells conditioned with phenol-red free DMEM containing 0.5% FBS for an additional 12 hours. Cells are then treated with increasing concentrations of PBIT (40 and 80 μM) or PBISe (2 and 4 μM) dissolved in phenol-red free DMEM (2 ml) containing 0.5% FBS for 72 hours. Culture supernatants are collected and total nitrite (nitrate+nitrite) measured by incubating 80 μL supernatant with enzyme cofactor mixture (10 μL) and nitrate reductase (10 μL) for 2 hours. Total nitrite is measured by the addition of Griess reagent-I and II (50 μL each). A nitrate standard curve (5-35 μM) is simultaneously prepared. Total nitrite present in media alone is subtracted from all experimental values and represented as micromolar nitrite produced following each treatment.

FIG. 1C is a graph showing total nitrate+nitrite levels measured in Caco-2 cells treated as described. Results show that 80 μM PBIT significantly reduces nitrate+nitrite levels compared to control PBS treated cells, which is indicative of iNOS inhibition, P<0.05; One-way ANOVA, Salvucci, O. et al., ibid.). PBISe reduces total nitrate+nitrite production in Caco-2 cells at lower concentrations, 2-4 μM, compared to PBIT as shown in FIG. 1C. Higher concentrations of PBISe are not used in this example since PBISe treatment kills>80% of cells at 2-4 μM.

Example 5

Viability and IC$_{50}$ Comparison of Normal Human Fibroblasts and Melanoma Cell Lines PBISe is compared to PBIT for effectiveness at killing melanoma cells using three independently derived melanoma cell lines, WM115, UACC 903 and 1205 Lu. 5×10$^3$ cells per well in 100 μL DMEM-10% FBS are grown in a 96-well plate for 36 or 72 hours, respectively for melanoma (UACC 903, 1205 Lu and WM115) and human fibroblast (FF2441) cell lines and treated with either PBS vehicle or increasing concentrations (3.5-21 μM) of PBIT, PBISe, PEIT or PEISe for 24 hours. Cellular viability compared to control treated cells is measured using the MTS assay (Promega, Madison, Wis.). IC$_{50}$ (μM) values for each compound in respective cell lines is determined from three independent experiments using GraphPad Prism version 4.01 (GraphPad, San Diego, Calif.), bars, SEM.

A representative example of the MTS analysis for UACC 903 is shown in FIG. 2A, demonstrating effectiveness of PBISe for decreasing melanoma cell viability compared to PBIT.

Dose response curves for agents are generated and IC$_{50}$ values determined (Table I). PBISe decreases viability of all three melanoma cell lines with an IC$_{50}$ range of 8-10 μM (Table I). PBISe is >10-fold more effective than PBIT, PEIT or PEISe at killing all three melanoma cell lines.

TABLE I

PBISe IC$_{50}$ (μM) Values For Melanoma Cell Lines

| Cell line | PBIT | PBISe | PEIT | PEIS |
|---|---|---|---|---|
| WM115 | >100 | 9.7 ± 1.4 | >100 | ~80 |
| UACC 903 | >100 | 8.1 ± 0.8 | >100 | >100 |
| 1205Lu | >100 | 9.8 ± 0.7 | >100 | >100 |

Example 6

Sensitivity of melanoma cells to PBISe is compared to normal cells. 5×10$^3$ normal human fibroblast, FF2441, and UACC 903 cells are plated in separate wells in 96 well plates in 100 μL DMEM containing 10% FBS and grown for 72 and 36 hours respectively. Exponentially growing cells are treated with increasing concentrations (2.5-100 μM) of PBISe for 2, 4, 6, 12, and 24 hours and IC$_{50}$ (μM) values determined. FIG. 2B shows that 2-5-fold higher PBISe concentrations are required to kill fibroblasts compared to melanoma cells. Thus, cultured cancer cells are 2-5 fold more sensitive to PBISe than normal cells.

Example 7

Inhibitory Effect on Colon Cancer Cell Lines

Viability of colon adenocarcinoma cells (Caco-2, HT 29, HCT 116, SW 480) and normal fibroblast cells (FF2441) treated with PBIT (1), PBISe (2), PEIT (3) or PEISe (4) is compared. The IC$_{50}$ value is evaluated by treating with increasing concentrations of PBIT, PEIT, PEISe (10-100 μM) or PBISe (1.6-50 μM) for 24-72 hours and the number of viable cell are quantified using MTS (Promega, Wis.).

Results are shown in Table II which indicates that the colon adenocarcinoma cells are 2-7 fold more sensitive to PBISe than normal cells (Table II). PBISe is potent at killing all four colon cancer cell lines with IC$_{50}$ range of 2.4-5.55 μM. PBIT shows an IC$_{50}$ value range >59-100 μM.

TABLE II

Inhibition of the Growth of Colon Cancer Cells - IC$_{50}$ Value - (μm)

| Cell Line | PBIT | PBISe | PEIT | PEISe |
|---|---|---|---|---|
| Fibroblast cells (FF2441) | >100 | 17.08 ± 0.59 | — | — |
| Colorectal adenocarcinoma (Caco-2) | 59.4 ± 3.83 | 2.4 ± 0.43 | >100 | 16 ± 2 |
| Colorectal adenocarcinoma HT-29* | >100 | 3.84 ± 0.44 | >100 | 21.92 ± 2.1 |
| Colorectal adenocarcinoma HCT-116 | >100 | 4.72 ± 0.44 | >100 | >100 |
| Colorectal adenocarcinoma | >100 | 5.55 ± 1.28 | >100 | >100 |

TABLE III

Inhibition Cancer Cells - IC$_{50}$ Value - (μm)

| Cell line | Cancer type | PBIT | PBISe | Fold increase in efficacy (PBIT/PBISe) |
|---|---|---|---|---|
| Caco-2 | Colorectal adenocarcinoma | 59.4 ± 3.8 | 2.4 ± 0.43 | ~24.7 |
| WM115 | Melanoma | >100 | 9.7 ± 1.4 | >10 |
| HT-1080 | Fibrosarcoma | >100 | 3.2 ± 0.61 | >31.2 |
| A549 | Lung carcinoma | >100 | 4.2 ± 0.58 | >23.8 |
| PC-3 | Prostate adenocarcinoma | >100 | 6.6 ± 0.95 | >15.2 |
| OVCAR-3 | Ovarian carcinoma | >100 | 5.3 ± 0.65 | >18.9 |
| MDA-MB-231 | Breast adenocarcinoma | >100 | 6.0 ± 0.54 | >16.7 |
| SW-480 | | | | |

Example 8

In Vitro Inhibitory Effect of PBIT and PBISe on Various Cancer Cell Types

Growth inhibitory effects on cultured cells from human vertical growth phase (VGP) melanoma cell line WM115, Lung adenocarcinoma (A549), fibrosarcoma (HT-1080), prostate adenocarcinoma (PC-3), ovarian carcinoma (OVCAR-3), and breast adenocarcinoma (MDA-MB-231) are plated in 96 well plates at a density of 5×10$^3$ cells/well in 100 μl media. The cells are treated 36 hours later with PBISe (0.19-100 μM), PBIT (10-100 μM), PEIT 10-100 μM), or PEISe (10-100 μM) for 24 h and cell viability measured using MTS assay. Dose response curves for each compound are generated and the IC$_{50}$ values (μM) determined using Graph-Pad Prism software. Each experiment is replicated at least 3 times and the average IC$_{50}$ (μM) values with standard error represented.

Table III shows IC$_{50}$ (μM) values calculated from dose response curves for PBIT and PBISe.

The IC$_{50}$ (μM) values calculated from dose response curves indicate that PBISe is >10 fold more potent at decreasing cell viability of all the cancer cell lines tested (A549, Caco-2, HT-1080, PC-3, OVCAR-3, MDA-MB-231, WM115) compared to PBIT. PBISe inhibits the growth of cancer cell viability and concentrations as low as 8-10 μM are sufficient to decrease the cell viability by 50% (Table III). At similar concentrations PBIT is not effective and IC$_{50}$ is observed to be more than 100 µM.

Example 9

Rates of cellular proliferation and apoptosis are examined in WM115, UACC 903 and 1205 Lu melanoma cells exposed to PBISe or PBIT.

Cellular proliferation and apoptosis rates are measured by seeding 5×10³ cells in 96-well plates, followed by treatment for 24 hours with PBISe or PBIT (0.5-10.5 µM). Proliferation and apoptosis rates are measured using a BrdU ELISA kit (Roche Applied Sciences, Indianapolis, Ind.) and Apo-ONE Homogenous caspase-3/7 Assay kit (Promega, Madison, Wis.), respectively, (Madhunapantula S V, et al.,. Cancer Res 2007; 67:3626-36).

PBISe more effectively inhibits cellular proliferation and increases apoptosis than PBIT in all three cell lines. 2 µM PBISe reduces UACC 903 cellular proliferative capacity by ~90% compared to PBS vehicle or PBIT treated cells. Compared to PBIT, increasing concentrations of PBISe elevated caspase-3/7 activity in a dose dependently manner up to 10.5 µM, which decreased at higher doses due to massive cell death (>80%) decreasing caspase-3/7 activity.

FIGS. 2C and 2D are representative graphs illustrating changes in proliferation and apoptosis in UACC 903 cells exposed to PBISe or PBIT. Results represent the average of 3 independent experiments; bars, SEM. Similar results are seen for WM115 and 1205 Lu cells.

Example 10

Cell Cycle Analysis

Cell cycle analysis is undertaken by growing 1.5×10⁶ melanoma cells in 100-mm culture dishes followed by treatment with PBIT or PBISe (3.5 to 21 µM) for 24 hours. Cells are collected and stained using propidium iodide (100 mg/mL; Sigma, St Louis, Mo.), 20 µg/mL Ribonuclease A (Roche, Indianapolis, Ind.) 3 µg/mL Triton X-100 dissolved in 0.1% (W/N) sodium citrate for 30 minutes at 4° C. (Krishan, A., J Cell Biol 1975; 66:188-93). Stained cells are analyzed using the FACScan analyzer (Becton Dickinson, San Jose, Calif.) and data processed using ModFit LT software (Verity Software House, Topsham, Me.).

Cell cycle analysis following PBISe but not PBIT exposure shows an increased sub G0/G1 population (FIG. 3A, results represent average of 2 independent experiments; bars, SEM) indicating elevated apoptosis and a ~3-fold increase in G2/M cells (FIGS. 3B and 3C), indicating a cell cycle arrest mediated by PBISe but not PBIT. Thus, PBISe inhibits proliferation by arresting cultured cells in the G2/M phase of the cell cycle and inducing apoptosis.

Example 11

Western Blot Analysis

PBISe modulates PI3 and MAP kinase signaling pathways regulating melanoma development. Since deregulated PI3 kinase (through overexpressed Akt3 and PTEN loss) and MAP kinase (through mutant $^{V600E}$B-Raf) signaling promotes melanoma development (Robertson, G. P., Cancer Metastasis Rev., 2005; 24:273-85; Stahl, J. M., et al., Res 2004; 64:7002-10; Sharma, A., et al., Cancer Res., 2006; 66:8200-9), effect of PBISe on these signaling cascades is examined by Western blot analysis of cellular lysates.

Melanoma cell line UACC 903 cells (1×10⁶) are treated with increasing concentrations (7-21 µM) of PBIT and PBISe for 24 hours and cell lysates examined by Western blot analysis Cell lysates are harvested by addition of lysis buffer containing 50 mM HEPES (pH 7.5), 150 mM NaCl, 10 mM EDTA, 10% glycerol, 1% Triton X-100, 1 mM sodium orthovanadate, 0.1 mM sodium molybdate, 1 mM phenylmethylsulfonyl fluoride, 20 µg/ml aprotinin, and 5 µg/ml leupeptin. Whole cell lysates are centrifuged ($\geq$10,000×g) for 10 minutes at 4° C. to remove cell debris. Protein concentrations are quantitated using the BCA assay (Pierce, Rockford, Ill.), and 30 µg of lysate loaded per lane onto NuPAGE Gels (Life Technologies, Carlsbad, Calif.). Following electrophoresis, samples are transferred to polyvinylidene difluoride membrane (Pall Corporation, Pensacola, Fla.). Blots are probed with antibodies to PRAS40 and phosphorylated PRAS40 (Thr246) (Invitrogen, Carlsbad, Calif.); antibodies to iNOS, cyclin D1, p27, p21, Erk2, α-enolase and secondary antibodies conjugated with horseradish peroxidase from Santa Cruz Biotechnology (Santa Cruz, Calif.); and antibodies to Akt3, phosphorylated-Akt (Ser473), phosphorylated-Erk 1/2 (Thr202/Tyr204), caspase-3 and cleaved PARP from Cell Signaling Technology (Danvers, Mass.). Immunoblots are developed using ECL (Pierce, Rockford, Ill.).

FIG. 4A is an immunoblot showing that, compared to PBIT, PBISe treatment inhibits Akt phosphorylation and decreases total Akt protein levels. This figure also shows phosphorylation of downstream Akt3 substrate PRAS40 is inhibited with associated increases in cleaved caspase-3 and PARP indicating elevated apoptosis as described in Madhunapantula, S. V. et al., Cancer Res 2007; 67:3626-36.

Figure 4C:
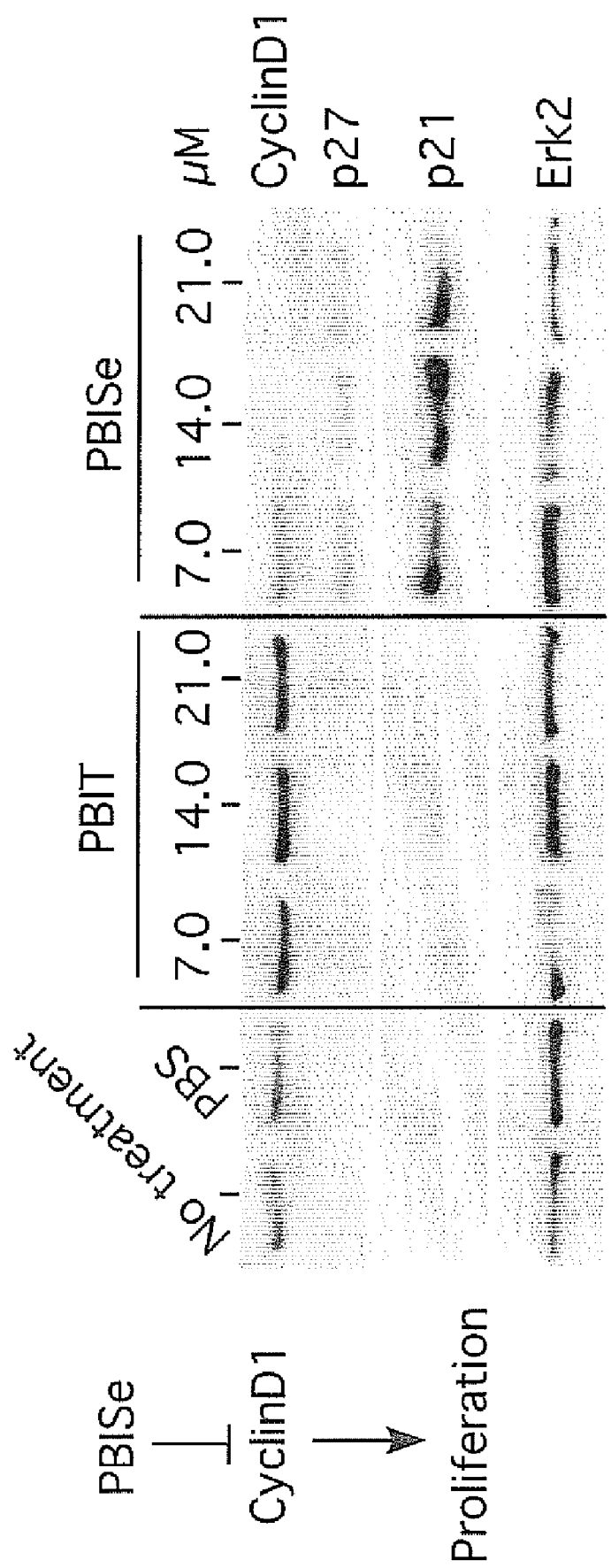
FIG. 4C is a reproduction of an image of an immunoblot illustrating changes in various proteins involved in cell proliferation signaling following treatment of cells with PBIT or PBISe.

UACC 903, WM115 and 1205 Lu cells have elevated MAP kinase pathway signaling due to presence of constitutively active $^{V600E}$B-Raf as described in Sharma, A., et al., Cancer Res., 2006; 66:8200-9; Sharma, A., et al., Cancer Res., 2005; 65:2412-21. Both PBIT and PBISe treatment result in increased pErk1/2 in these cell lines, indicating increased MAP kinase pathway activity following treatment, (representative example; FIG. 4B). Increased MAP kinase activity can be inhibitory to cells if activity of this pathway is overly active as described in Cheung, M., et al., Cancer Res., 2008, 68:3429-3439; and Dhomen, N. et al., Cancer Cell, 2009, 2009, 15, 294-303). FIG. 4B shows that increased Erk1/2 following PBIT treatment elevates iNOS expression as described in Ellerhorst, J. A., et al., Oncogene 2006; 25:3956-62; Tunctan, B., et al., Pharmacol. Res., 2007; 56:56-64. FIG. 4C shows that PBIT does not alter cyclin D1 levels. In contrast, PBISe reduces expression of cyclin-D1 and increases p27 as well as p21 levels in three cell lines, shown in the representative example immunoblot in FIG. 4C. It is believed that this difference is due to PBISe-mediated inhibition of Akt3 activity, which can increase MAP kinase activity in melanoma cells by decreasing phosphorylation of $^{V600E}$B-Raf, which causes excessively high MAP kinase pathway activity (Cheung, M., et al., ibid). Under this circumstance, PBISe inhibits Akt3 activity making it unable to phosphorylate $^{V600E}$B-Raf at serines 364 and 428 to reduce activity of $^{V600E}$B-Raf and downstream MAP kinase pathway to levels that promote rather than inhibit proliferation (Cheung, M., et al., ibid). The result is elevated MAP kinase activity to inhibitory levels, which decreases cyclin-D1 expression and increases p27 as well as p21 (Cheung, M., et al., ibid). Thus, PBISe-mediated inhibition of Akt3 pathway signaling increases MAP kinase activity to inhibitory levels, thereby increasing cellular apoptosis and decreasing cellular proliferation.

Example 12

Tumorigenicity Assessments and Measurement of Proliferation and Apoptosis Rates Effectiveness of PBISe for inhibiting melanoma tumor development is evaluated on preexisting tumors in nude mice.

Tumor kinetics are measured by subcutaneous injection of $5\times10^6$ UACC 903 or $2.5\times10^6$ 1205 Lu cells in 0.2 ml of DMEM containing 10% FBS above left and right rib cages of 4-6 week old female nude mice (Harlan Sprague Dawley, Indianapolis, Ind.). Six days later, a fully vascularized tumor has developed and mice are randomly placed in control DMSO or experimental (PBIT or PBISe) groups (n=5 animals; 10 tumors total) followed by i.p. treatment with PBIT (0.315 μmoles) or PBISe (0.315 moles; equivalent to 2.5 ppm selenium per 20 g mouse) on Monday, Wednesday and Friday for 3 weeks. Dimensions of developing tumors and body weight are measured.

For mechanistic studies, $5\times10^6$ UACC 903 cells are injected subcutaneously into nude mice generating tumors of the same size developing at parallel time points. 6-days later mice are treated i.p. with DMSO vehicle, PBIT or PBISe (0.315 mmoles each) on alternate days up to day 15. Size and time matched tumors are harvested at days 9, 11, 13, and 15 to assess changes in cell proliferation and apoptosis. A small portion of tumor is flash frozen in liquid $N_2$ for caspase-3/7 activity analysis and processed by pulverizing into powder and adding protein lysis buffer (600-800 μl per 50 mg powder, 50 mM Tris-HCl, pH 7.5 containing 0.1% Triton X-100, 1 mM EDTA, 1 mM EGTA, 50 mM sodium fluoride, 10 mM sodium β-glycerol phosphate, 5 mM sodium pyrophosphate, 1 mM activated sodium orthovanadate, protease inhibitor cocktail and 0.1% (v/v) 2-mercaptoethanol) followed by repeated centrifugation (10,000×g). Protein concentration is quantitated using Bio-Rad protein assay reagent (Bio-Rad laboratories, Hercules, Calif.) and analyzed by Western blotting.

For caspase-3/7 activity determination, 100 μg of protein lysate is incubated with a Rhodamine-110 conjugated caspase-3/7 substrate (Z-DEVD) for 1-2 hours and fluorescence (485 nm excitation and 520 nm emission) measured in a SPECTRAmax M2 plate reader. Cell proliferation is measured in formalin-fixed, paraffin-embedded tumor sections using purified mouse anti-human Ki-67 from PharMingen (San Diego, Calif.). A minimum of 6 different tumors with 4-6 fields per tumor is analyzed and results represented as the average ±SEM.

Figure 5A:
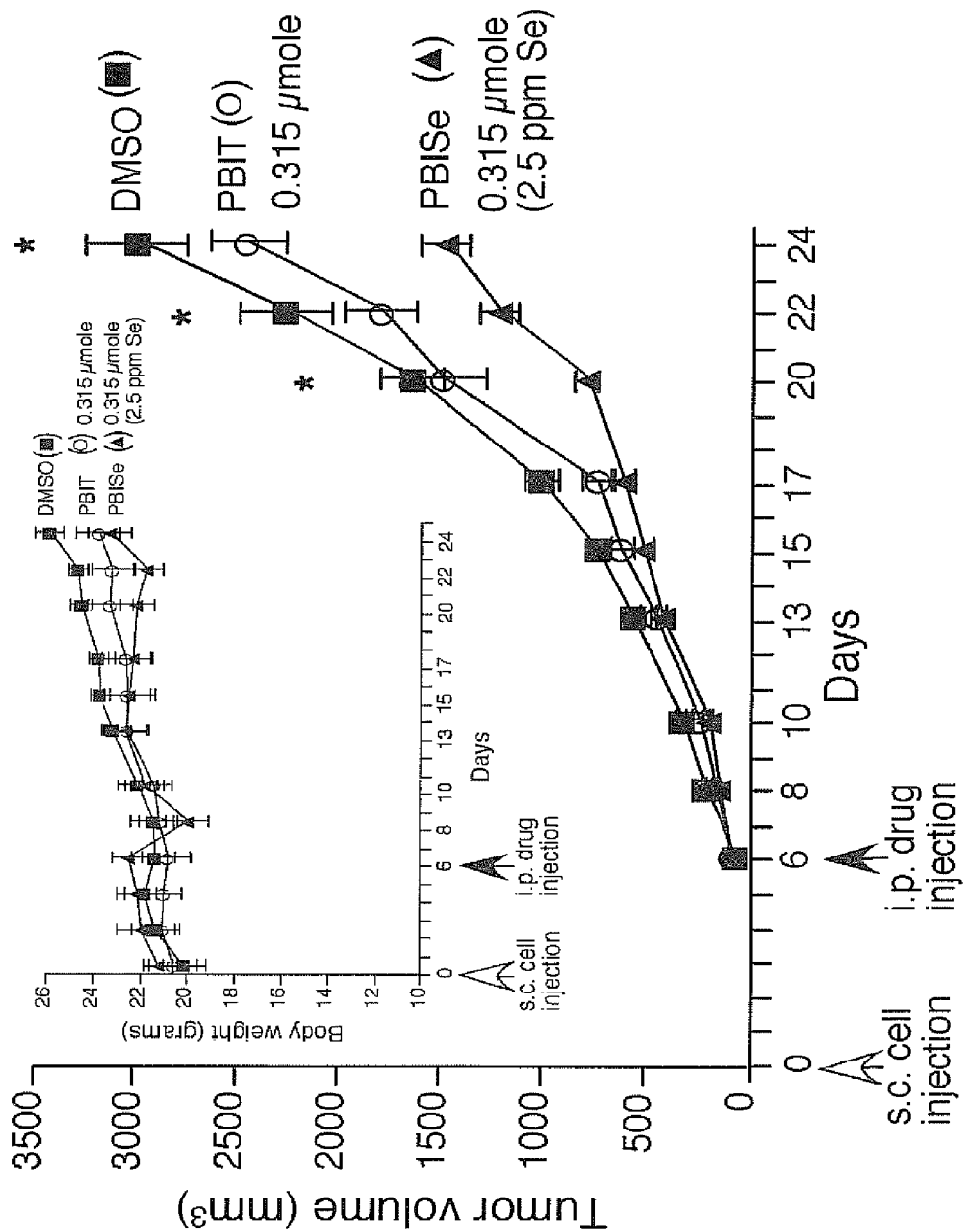
FIG. 5A shows two graphs illustrating the effects of PBIT and PBISe on tumor volume and body weight in mice.

FIG. 5A and FIG. 5B show results indicating that treatment with PBISe but not PBIT significantly reduces 1205 Lu and UACC 903 tumor development by ~30-50%. Shown are average values obtained from 10 tumors (n=5 animals), bars; ±SEM. Compared to PBIT or DMSO vehicle, PBISe significantly decreased tumor development beginning from day 17 ($p<0.001$; Two-way ANOVA). At day 24, difference between control DMSO or PBIT compared to PBISe treated tumor volumes is ~50% for 1205 Lu cells (5A) and ~30% for UACC 903 cells (5B). No significant difference is observed body weight during treatment indicating negligible toxicity.

Example 13

Systemic Toxicity Assessments

Figure 5C:
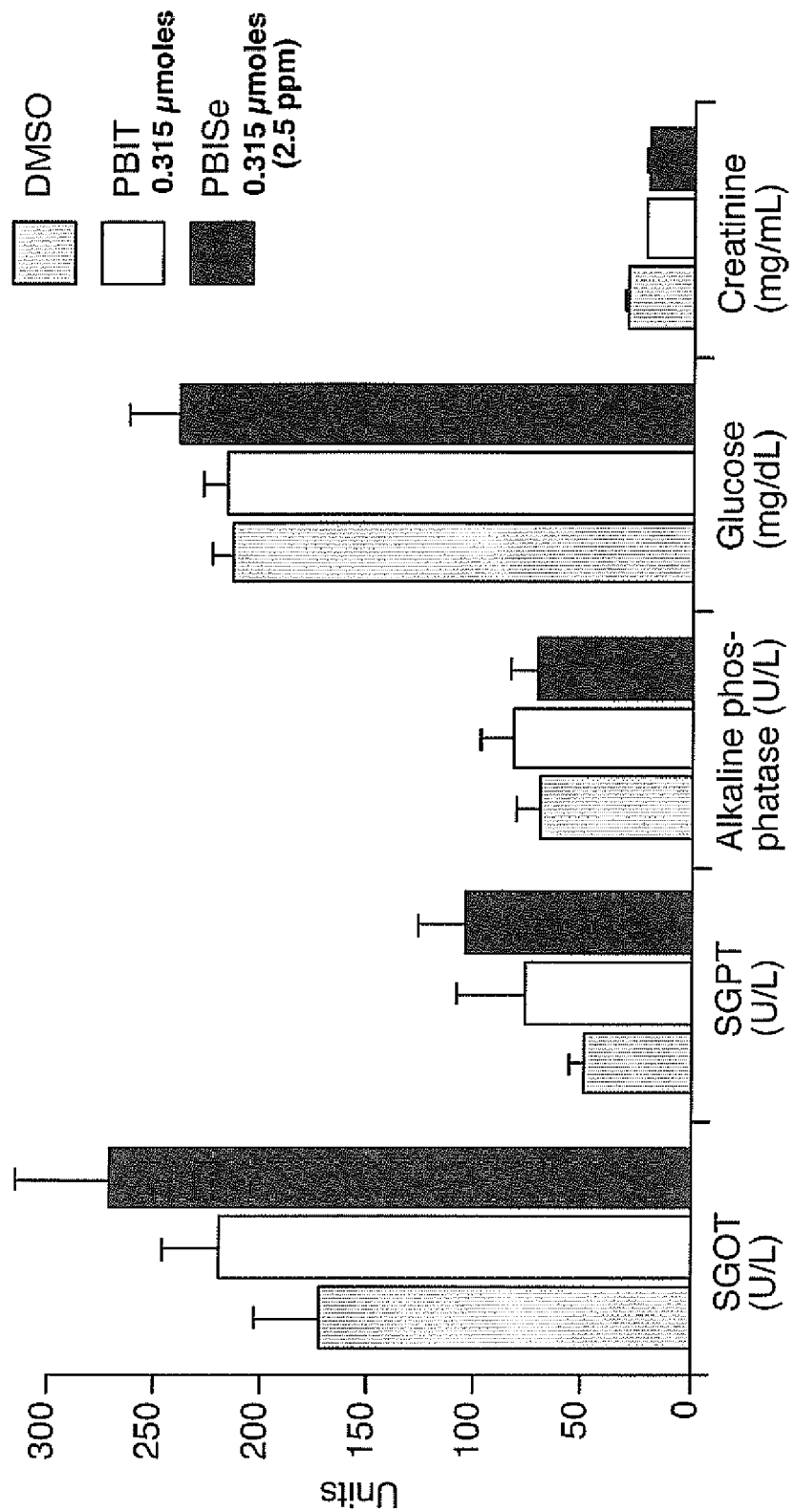
FIG. 5C is a graph showing effects of treatment with PBIT or PBISe on various indicators of toxicity in mice.

Systemic toxicity of PBISe in animals is evaluated in nude mice. Mice are exposed to PBISe or PBIT (0.315 μmoles each), or vehicle DMSO, 3 times per week and animals weighed to ascertain possible toxicity. 4-6 week old female nude mice (Harlan Sprague Dawley, Indianapolis, Ind.) are injected i.p. with either control DMSO vehicle, PBIT or PBISe (0.315 μmoles each) for 3 weeks by following the regime used for tumorigenicity. Blood is then collected from each animal in plasma separator tubes with lithium heparin (BD Microtainer, BD, Franklin Lakes, N.J.) following cardiac puncture and analyzed for SGOT, SGPT, alkaline phosphatase, glucose and creatinine to ascertain liver, heart, kidney and pancreas related toxicity. For morphological examination of blood cells, whole blood is collected in microtainer tubes containing $K_2$EDTA (BD Microtainer, BD, Franklin Lakes, N.J.) and RBC, WBC, lymphocytes, monocytes, eosinophils, platelets, total hemoglobin and hematocrit percentage analyzed. Blood is also microscopically examined for segregates, polychromatin bodies, and smudge cells. A portion of vital organs—liver, heart, kidney, intestine, pancreas and adrenal—from each animal is formalin fixed and paraffin-embedded to examine for toxicity-associated changes in cell morphology and organization following H&E staining. No significant difference in body weight between PBISe treated animals and controls is observed suggesting negligible toxicity, as shown in the insert graphs in FIGS. 5A & 5B. Furthermore, blood parameters (SGOT, SGPT, alkaline phosphatase, blood urea, glucose and creatinine) indicative of systemic toxicity did not detect significant liver, kidney or cardiac related toxicity as shown in FIG. 5C. Histological examination of H&E stained vital organ sections reveal that PBISe treatment did not significantly change cell morphology or organ structure. Thus, PBISe treatment has negligible associated systemic toxicity at the concentrations examined.

Example 14

PBISe Induces Cellular Apoptosis in the Tumor Environment

Figure 5D:
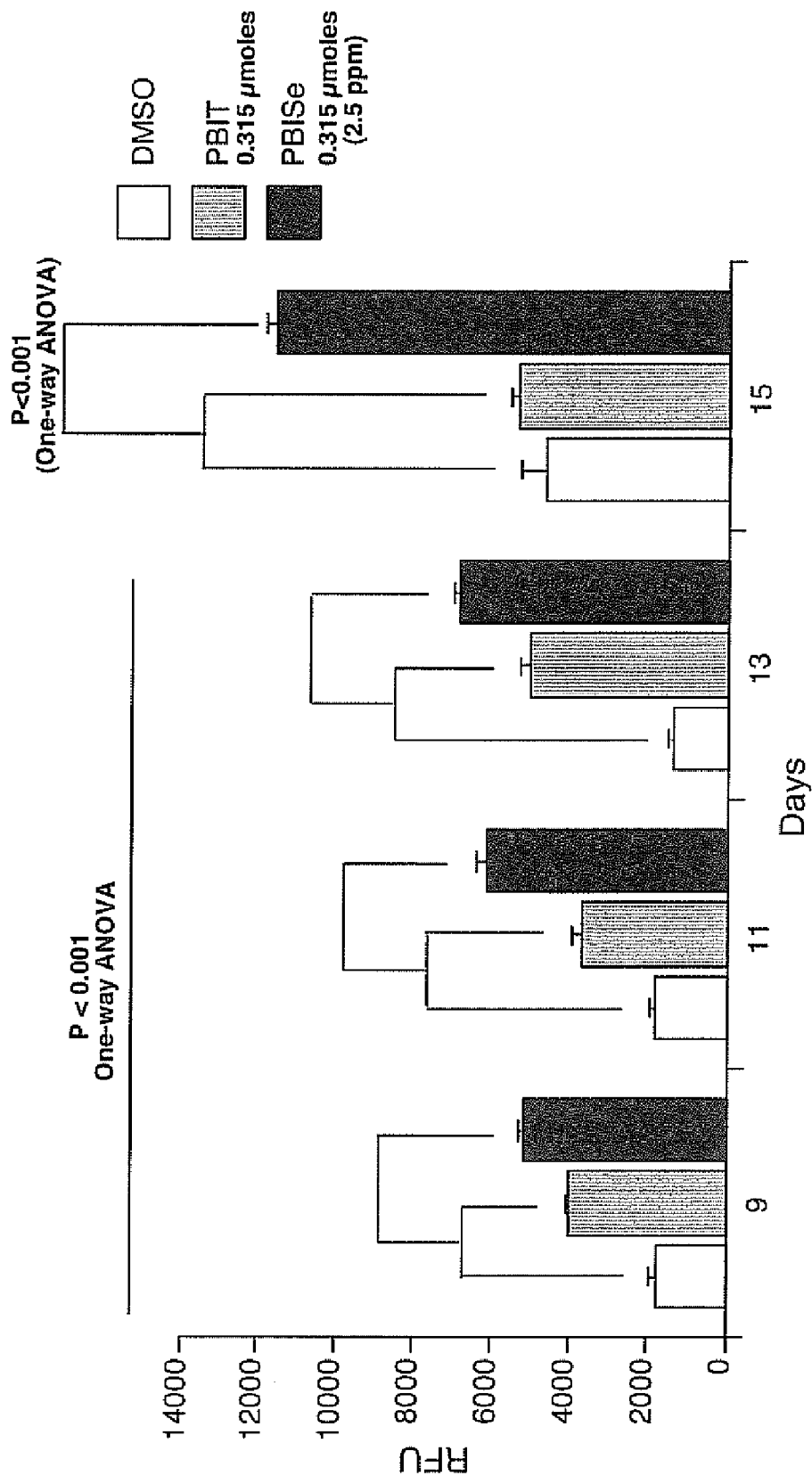
FIG. 5D is a graph showing effects of treatment with PBIT or PBISe on an indicator of apoptosis of tumor cells in mice.

Rates of tumor cell apoptosis and proliferation are compared in size and time matched tumors following PBISe, PBIT or control DMSO vehicle treatment. Mice bearing tumors matched for size and time of development are injected i.p. with PBIT and PBISe (0.315 μmoles) or DMSO (50 μl) vehicle starting 7 days after subcutaneous injection of cell and on alternate days thereafter up to day 15. Tumors are removed from euthanized mice on days 9, 11, 13, and 15 for measurement of caspase-3/7 activity using the Apo-ONE homogeneous caspase-3/7 assay kit. Progressively, statistically higher levels of apoptosis (caspase-3/7 activity) are observed from tumors at days 9-15, with a 2-fold difference measured at day 15. Magnitude of apoptosis, assessed by caspase 3/7 activities, in tumor protein lysates are shown in FIG. 5D. UACC 903 tumors treated with PBISe had double the caspase 3/7 activity by day 15 observed in tumors treated with PBIT or DMSO vehicle (FIG. 5D, $p<0.05$; One-way ANOVA, Values represent average from 3 independent experiments, bars, ±SEM). In contrast, no statistically significant difference is observed in rates of cellular proliferation, which remained between 1-2% for PBISe and PBIT treated tumors. However, PBISe and PBIT treated tumors have 2-3 fold fewer proliferating cells than animals exposed to control DMSO. Thus, PBISe inhibits melanoma tumor development by increasing apoptosis levels compared to PBIT and leads to negligible differences in proliferation rates.

Example 15

Statistical Analysis

Statistical analysis is undertaken using the One-way or Two-way ANOVA followed by the Turkey's or Bonferroni's post hoc tests. Results are considered significant at a p-value of <0.05.

Example 16

In Vitro Inhibition of PI3 Kinase Signaling in Colon Cancer Cell Lines Using PBISe For additional Western blot analysis, Caco-2 cell cell lysates are harvested by addition of lyses buffer containing 50 mM HEPES (pH 7.5), 150 mM NaCl, 10 mM EDTA, 10% glycerol, 1% Triton X-100, 1 mM sodium orthovanadate, 0.1 mM sodium molybdate, 1 mM phenylmethylsulfonyl fluoride, 20 μg/ml aprotinin, and 5 μg/ml leupeptin. Whole cell lysates are centrifuged ($\geq$10,000×g) for 10 minutes at 4° C. to remove cell debris. Protein concentrations are quantitated using the BCA assay (Pierce; Rockford, Ill.), and 30 μg of lysate loaded per lane onto NuPAGE Gels (Life Technologies, Inc. Carlsbad, Calif.). Following electrophoresis, samples are transferred to polyvinylidene difluoride (PVDF) membrane (Pall Corporation, Pensacola, Fla.) and the blots probed with antibodies according to each supplier's recommendations: antibodies to PRAS40 and phosphorylated PRAS40 from Invitrogen (Invitrogen Corporation, Carlsbad, Calif.); antibodies to cyclin D1, p27, p21, and Erk2 from Santa Cruz Biotechnology (Santa Cruz, Calif.); and antibodies to Akt2, phosphorylated-Akt (Ser473), phosphorylated-Erk 1/2 and cleaved PARP from Cell Signaling Technology (Danvers, Mass.). Secondary antibodies conjugated with horseradish peroxidase are obtained from Santa Cruz Biotechnology (Santa Cruz, Calif.). Immunoblots are developed using the enhanced chemiluminescence (ECL) detection system (Pierce Biotechnology, Rockford, Ill.) (FIGS. 6A and 6B).

To elucidate the effects of PBISe and PBIT on molecular targets that are critical in the development of colon cancer, effects on PI3 kinase and downstream targets are examined. FIG. 6 shows effect of PBISe on PI3 kinase signaling using Western blot analysis. A decreased pAkt and Akt2 levels that are relatively specific for colon cancer, and a downstream pPRAS40 level accompanied by an increase in cleaved PARP, an apoptosis marker, demonstrating decreased PI3 kinase activity upon exposure to PBISe but not PBIT. Therefore, PBISe significantly inhibits PI3 kinase and pAkt signaling pathways in colon cancer cells to increase apoptosis and decrease proliferation. PBISe significantly inhibits PI3 kinase signaling and pAkt signal in colon cancer cells to increase apoptosis and decrease proliferation.

Example 17

Effect of Topical Inventive Composition Application on Melanoma Tumor Growth—in Skin Reconstructs Generation of skin containing melanocytic lesions is briefly described. To create skin in a culture dish, human fibroblasts, are trypsinized and resuspended in 10% reconstitution buffer, 10% 10×DMEM (Mediatech, Herndon, Va.), 2.4 microliters/ml of 10 M NaOH, and 80% collagen I (BD Discovery Labware Inc., Bedford, Mass.) at a concentration of $2.5 \times 10^5$ cells/ml on ice (Ozbun Mass., Meyers C. Jr Virol 1996, 70: 5437-46.). Mixture is then aliquoted into 6 or 12 well plates and incubated at 37° C. for 3 hours. E-media is added to each well to equilibrate the dermal matrix (Wu Y J, Parker L M, Binder N E, et al., Cell 1982, 31: 693-703.). After two days of growth, keratinocytes and melanoma cells (WM35-GFP or UACC 903-GFP) are trypsinized and resuspended at a 1:10 ratio of melanoma cells (nucleofected or untreated) to keratinocytes in E-media. One milliliter of cell suspension is added to each well on top of the dermal layer. Following two days growth, reconstructed skin is transferred onto wire grids and fed via diffusion from E-media below the platforms.

Skin reconstructs containing melanoma cells are treated topically with increasing concentrations (5, 10, 15 and 20 μM in 200 μL PBS) of PBIT or PBISe. Eight days later control vehicle PBS treated, PBIT and PBISe exposed skins are fixed in paraformaldehyde and stored in 0.5% EDTA. FIG. 7A shows images of sections from each group stained with hematoxylin and eosin and the cell morphology and overall structural integrity of treated and control sections is compared. The images in FIG. 7A show intact morphology of constituent cells after treating with 20 uM PBISe, indicating no toxicity.

Skin reconstructs containing WM35 melanoma cell tumors expressing green fluorescent protein (GFP) or UACC 903 melanoma cell tumors expressing GFP are generated in culture. Beginning on day 8 of culture, the reconstructed skins containing melanoma tumors are treated with increasing concentrations of PBISe (5, 10, 15 and 20 μM) or PBIT (15 and 20 μM) in 200 μL of vehicle PBS for 8 days and the size of developing tumors, in terms of area occupied by GFP, is measured using fluorescence microscopy.

The data show that PBISe treatment decreased the tumor sizes in a dose dependent manner in both WM35 and UACC 903 tumors. At 15 and 20 μM PBISe concentration a significant difference is measured (~80-90%, P<0.05, One-way ANOVA) compared to vehicle PBS control and compared to PBIT treated skins. FIG. 7B shows a graph of the area occupied by tumor nodules in the reconstructed skin containing WM35 GFP cells after 8 days of topical treatment with 5, 10, 15 or 20 μM PBISe or 15 or 20 μM PBIT. FIG. 7B also shows representative fluorescent micrographs of GFP in cells treated as indicated for 8 days. The results show that topical PBISe inhibits early melanoma development.

FIG. 7C shows a graph of the area occupied by tumor nodules in the reconstructed skin containing UACC 903 GFP cells after 8 days of topical treatment with 5, 10, 15 or 20 μM PBISe or 15 or 20 μM PBIT. FIG. 7C also shows representative fluorescent micrographs of GFP in cells treated as indicated for 8 days. The results show that topical PBISe inhibits metastatic melanoma development.

Example 18

Effect of Topical Inventive Composition Application on Melanoma Tumor Growth—In Vivo UACC 903 melanoma cells ($0.25 \times 10^5$/site) are subcutaneously injected into left and right flanks of 4-6 weeks old female nude mice (n=4) and 24 h later PBIT, PBISe (0.0945 umoles, 1.5 ppm selenium equivalent to 5.12 mg/kg body weight) or vehicle control (acetone) is applied topically for 29 days. Sizes of developing tumors are measured and average sizes ±S.E.M. (in mm$^3$) plotted. A minimum of 5 mice per group is used for the topical treatment.

FIG. 8A shows graphs indicating that there is a significant (P<0.05) 50% decrease in tumor volume between vehicle acetone treated mice or PBIT treated mice compared with PBISe treated mice observed beginning from day 17 through the end of the treatment (day 29) indicating PBISe but not PBIT is effective at preventing melanoma tumors growth.

FIG. 8B is a graph showing no detectable differences between these groups indicating topical application of PBIT or PBISe every day is not toxic to mice.

Blood collected from the control and experimental animals, at the end of treatment (day 29), are analyzed for SGOT, SGPT (representing liver and cardiac toxicity) and alkaline phosphatase (for kidney and cardiac toxicity). Additionally, concentrations of metabolites (glucose, creatinine, urea nitrogen and total protein) in serum are also determined. FIG. 8C is a graph showing no significant differences between control and experimental groups demonstrating no associated toxicity with the every day topical application of PBISe.

Any patents or publications mentioned in this specification are incorporated herein by reference to the same extent as if each individual publication is specifically and individually indicated to be incorporated by reference. U.S. Provisional Patent Application Ser. No. 61/044,788, filed Apr. 14, 2008, is incorporated herein by reference in its entirety. U.S. patent application Ser. No. 12/423,366, filed Apr. 14, 2009, is incorporated herein by reference in its entirety.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating a subject having or at risk of having melanoma, comprising:
  administering a therapeutically effective amount of a composition comprising a compound having the structural formula:

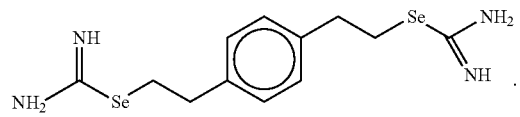

2. The method of claim 1, wherein the composition is formulated for topical application.

3. The method of claim 1, wherein the subject is human.

4. The method of claim 1, wherein the melanoma is characterized by dysregulation of Akt, iNOS or MAP kinase.

5. The method of claim 1, wherein the melanoma is characterized by dysregulation of Akt3.

6. The method of claim 1, wherein administering the therapeutically effective amount of the composition to a subject detectably increases apoptosis and/or decreases proliferation of cells of the melanoma.

7. The method of claim 1, further comprising administration of an adjunct anti-cancer treatment.

8. The method of claim 1, wherein the composition is administered topically.

* * * * *

UNITED STATES PATENT AND TRADEMARK OFFICE
CERTIFICATE OF CORRECTION

PATENT NO. : 8,309,541 B1
APPLICATION NO. : 13/107494
DATED : November 13, 2012
INVENTOR(S) : Gavin P. Robertson et al.

Page 1 of 1

It is certified that error appears in the above-identified patent and that said Letters Patent is hereby corrected as shown below:

Column 1, lines 14-20: Replace

"The invention was made with government support under Contract No. HHSN261200566003C awarded by the U.S. Public Health Service, Contract No. NO2-CB-56603 awarded by the U.S. National Institutes of Health National Cancer Institute; and Contract No. CA-127892-01A awarded by the U.S. National Institutes of Health. The government has certain rights in the invention."

with

--This invention was made with government support under Grant Nos. CB056603, CA127892, CA136667 and HHSN261200566003C awarded by The National institutes of Health. The Government has certain rights in the invention.--

Signed and Sealed this
Twenty-sixth Day of February, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,309,541 B1
APPLICATION NO. : 13/107494
DATED : November 13, 2012
INVENTOR(S) : Gavin P. Robertson et al.

Page 1 of 1

It is certified that error appears in the above-identified patent and that said Letters Patent is hereby corrected as shown below:

In the Specification:

At column 13, line number 40, After I, Insert --II--

At column 18, line number 5, After HTB-37, Insert --HCT-116--

At column 19, line number 60, Delete "$H_1$", Insert --$H_{19}$--

At column 20, line number 2, Delete "H-HMR", Insert --H-NMR--

Signed and Sealed this
First Day of July, 2014

Michelle K. Lee
*Deputy Director of the United States Patent and Trademark Office*